United States Patent [19]

Afeyan et al.

[11] Patent Number: 5,019,270

[45] Date of Patent: May 28, 1991

[54] PERFUSIVE CHROMATOGRAPHY

[75] Inventors: Noubar B. Afeyan, Brookline, Mass.; Fred E. Regnier, West Lafayette, Ind.; Robert C. Dean, Jr., Norwich, Vt.

[73] Assignee: PerSeptive Biosystems, Inc., Cambridge, Mass.

[21] Appl. No.: 595,661

[22] Filed: Oct. 9, 1990

Related U.S. Application Data

[63] Continuation of Ser. No. 376,885, Jul. 6, 1989, abandoned.

[51] Int. Cl.$^5$ .............................................. B01D 15/08
[52] U.S. Cl. .................................... 210/656; 210/635; 210/198.2; 55/67; 55/386; 530/413; 530/417
[58] Field of Search ...................... 210/635, 656, 198.2; 55/67, 386; 530/413, 417; 436/161

[56] References Cited

U.S. PATENT DOCUMENTS

| | | | |
|---|---|---|---|
| 3,862,030 | 1/1975 | Goldberg | 210/24 |
| 4,102,746 | 7/1978 | Goldberg | 195/63 |
| 4,186,120 | 1/1980 | Ugelstad | 260/29.6 R S |
| 4,384,957 | 5/1983 | Crowder, III et al. | 210/656 |
| 4,496,461 | 1/1985 | Leeke et al. | 210/198.2 |
| 4,512,897 | 4/1985 | Crowder, III et al. | 210/656 |
| 4,604,198 | 8/1986 | Dailey et al. | 210/198.2 |

OTHER PUBLICATIONS

W. M. Deen, 33 Aiche J. 9:1409–1425 (1987).
Lloyd et al., "Affinity and Ion Exchange Chromatographic Supports for High Performance Biological Separations", presented at the International Conference on Separations for Biotechnology, University of Reading, United Kingdom, Sep. 15–18, 1987.
Lloyd et al., "Polymeric Anion Exchange Columns for the HPLC Analysis of Large Biological Solutes (Proteins)", presented at the 39th Pittsburgh Conference and Exposition on Analytical Chemistry and Applied Spectroscopy, New Orleans, Louisiana, Feb. 22–26, 1988.
McConville et al., "Influence of Pore Size/Ionic Capacity on the Separation of Small and Large Biomolecules When Using Polymeric Anion Exchange Media", a publication of Polymer Laboratories, Inc., Amherst, Mass.
R. Kunin, "Pore Structure of Macroreticular Ion-Exchange Resins", Ion Exch. Proc. Ind., Pap. Conf., pp. 10–15 (1970).
Millar et al., "Solvent-Modified Polymer Networks: Part I", J. Chem. Soc., pp. 218–225 (1963).
Sederel et al., J. Appl. Polymer Sci. 17:2835–2846 (1973).
Jacobelli et al., J. Appl. Polymer Sci. 23:927–939 (1979).
Jacobelli et al., 80 Die Angewandte Makromolekulare Chemie 1167:31–51 (1979).
"High Performance Columns and Media for Today's Life Scientists", Polymer Labortories, Ltd. publication (Shropshire, England) (1989), pp. 1–9.
L. B. Bangs, "Uniform Latex Particles", a publication of Seradyn, Inc., pp. 5–9 (1987).

(List continued on next page.)

Primary Examiner—Ernest G. Therkorn
Attorney, Agent, or Firm—Testa, Hurwitz & Thibeault

[57] ABSTRACT

Disclosed are chromatography methods and matrix geometries which permit high resolution, high productivity separation of mixtures of solutes, particularly biological materials. The method involves passing fluids through specially designed chromatography matrices at high flow rates. The matrices define first and second interconnected sets of pores and a high surface area for solute interaction in fluid communication with the members of the second set of pores. The first and second sets of pores are embodied, for example, as the interstices among particles and throughpores within the particles. The pores are dimensioned such that, at achievable high fluid flow rates, convective flow occurs in both pore sets, and the convective flow rate exceeds the rate of solute diffusion in the second pore set. This approach couples convective and diffusive mass transport to and from the active surface and permits increases in fluid velocity without the normally expected bandspreading.

34 Claims, 24 Drawing Sheets

OTHER PUBLICATIONS

Lieto et al., *Chemtech* 46-53 (Jan. 1983).
Ugelstad et al., "Effect of Additives on the Formation of Monomer Emulsions and Polymer Dispersions", *Emulsion Polymerization* 383-413 (1982).
Horak et al., 117 *Die Angewandte Makromolekulare Chemie* 1875:117-129 (1983).
Yau et al., *Modern Size-Exclusion Liquid Chromatography*, a Wiley-Interscience Publication (New York: John Wiley & Sons, 1978) pp. 77-95.
van der Wiel et al., "Continuous Adsorption in Biotechnology", a preprint containing results presented at the 1986 Engineering Foundation Conference, Uppsala, Sweden.
J. Calvin Giddings, *Dynamics of Chromatography*, vol. 1 (New York: Marcel Decker, Inc.) (1965), pp. 1-323.
Giddings et al., 10 *Macromolecules* 2:443-449 (1977).
van Kreveld et al., *J. Chromatogr.* 149:71-91 (1978).
Guttman et al., 3 *Macromolecules* 5:681-691 (1970).
Klein et al., 14 *Macromolecules* 5:1411-1422 (1981).
Chiantore et al., 5 *J. of Liquid Chromatogr.* 4:643-667 (1982).
J. Calvin Giddings, *Adv. Chromatogr.* 20:217-258 (1982).
4 *BioChromatography* 1:25 (Jan./Feb. 1989), reference to oral presentation delivered at 12th Intl. Symposium on Column Liquid Chromatography, Jun. 19-24, 1988, in Washington, DC.
Kun et al., *J. Polymer Sci.* 16:1457-1469 (1967).
Kun et al., *J. Polymer Sci.* 6:2689-2701 (1968).
Rounds "Poly(styrene-Divinylbenzene)-Based Strong Anion-Exchange Packing Material for High-Performance Liquid Chromatography of Proteins", Journal of Chromatography, 397(1987) pp. 25-38.
Snyder, Introduction to Modern Liquid Chromatography, John Wiley & Sons, Inc. 1979, pp. 27-31, 56-58, 484-486, and 493-499.

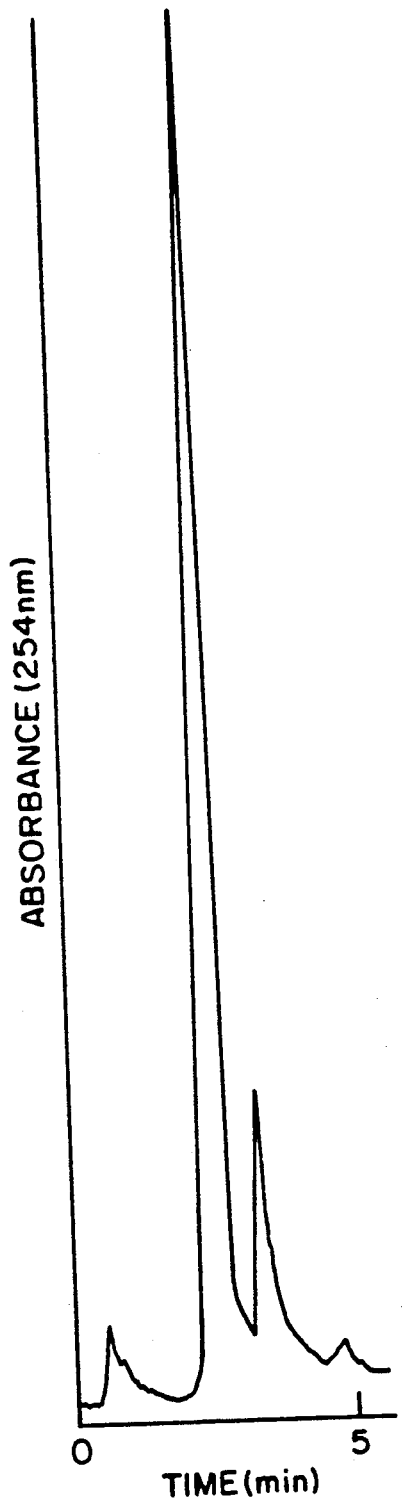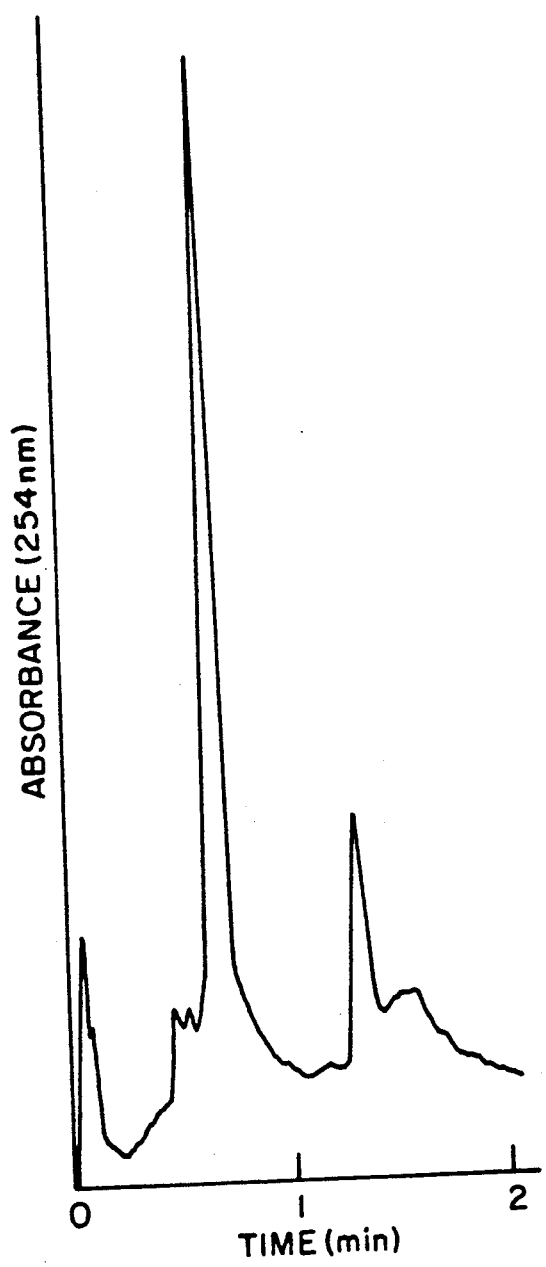
FIG. 17A
FIG. 17B

PERFUSIVE CHROMATOGRAPHY

This application is a continuation of application Ser. No. 376,885, filed July 6, 1989, now abandoned.

BACKGROUND OF THE INVENTION

This invention relates to methods and materials for conducting very high efficiency chromatographic separations, i.e., adsorptive chromatography techniques characterized by both high resolution and high throughput per unit volume of chromatography matrix. More specifically, the invention relates to novel geometries for matrices useful in chromatography, particularly preparative chromatography, and to methods for conducting chromatographic separations at efficiencies heretofor unachieved.

The differences in affinities of individual solutes for a surface based on charge, hydrophobic/hydrophilic interaction, hydrogen bonding, chelation, immunochemical bonding, and combinations of these effects have been used to separate mixtures of solutes in chromatography procedures for many years. For several decades, liquid chromatography (LC) has dominated the field of analytical separation, and often has been used for laboratory scale preparative separations. Liquid chromatography involves passing a feed mixture over a packed bed of sorptive particles. Subsequent passage of solutions that modify the chemical environment at the sorbent surface results in selective elution of sorbed species. Liquid flows through these systems in the interstitial space among the particles.

The media used for liquid chromatography typically comprises soft particles having a high surface area to volume ratio. Because of their many small pores having a mean diameter on the order of a few hundred angstroms (Å) or less, 95% or more of the active surface area is within the particles. Such materials have been quite successful, particularly in separation of relatively small chemical compounds such as organics, but suffer from well-recognized limits of resolution for larger molecules. Liquid chromatography materials also are characterized by operational constraints based on their geometric, chemical, and mechanical properties. For example, soft LC particles cannot be run at pressure drops exceeding about 50 psi because the porous particles are easily crushed.

Recently, high performance liquid chromatography (HPLC) has become popular, particularly for analytical use. Instead of employing soft, particulate, gel-like materials having mean diameters on the order of 100 $\mu$m, HPLC typically employs as media 10 to 20 $\mu$m rigid porous beads made of an inorganic material such as silica or a rigid polymer such as a styrene divinylbenzene copolymer. HPLC allows somewhat faster and higher resolution separations at the expense of high column operating pressure drops.

Products emerging from the evolving biotechnology industry present new challenges for chromatography. Typically, these products are large and labile proteins having molecular weights within the range of $10^4$ to $10^6$ daltons. Such products are purified from mixtures which often contain hundreds of contaminating species including cell debris, various solutes, nutrient components, DNA, lipids, saccharides, and protein species having similar physicochemical properties. The concentration of the protein product in the harvest liquor is sometimes as low as 1 mg/l but usually is on the order of 100 mg/l. The larger proteins in particular are very fragile, and their conformation is essential to their biological function. Because of their complex structure and fragility, they must be treated with relatively low fluid shear, and preferably with only minimal and short duration contact with surfaces. The presence of proteases in the process liquor often mandates that purification be conducted as quickly as possible.

The major performance measures of chromatography techniques are productivity and peak resolution. Productivity refers to specific throughput. It is a measure of the mass of solute that can be processed per unit time per unit volume of chromatography matrix. Generally, productivity improves with increases in 1) the surface area per unit volume of the matrix, 2) the rate of solute mass transfer to the sorbent surface, 3) the rate of adsorption and desorption, and 4) the fluid flow velocity through the matrix.

Resolution is a measure of the degree of purification that a system can achieve. It is specified by the difference in affinity among solutes in the mixture to be separated and by the system's inherent tendency toward dispersion (bandspreading). The former variable is controlled by the nature of solutes in the process liquor and the chemical properties of the interactive surface of the chromatography medium. Bandspreading is controlled primarily by the geometry of the chromatography matrix and the mass transfer rates which obtain during the chromatography procedure. Resolution is improved as theoretical plate height decreases, or the number of plates increases. Plate height is an indirect measure of bandspreading relating to matrix geometric factors which influence inequities of flow, diffusion, and sorption kinetics.

It obviously is desirable to maximize productivity and to minimize bandspreading in a matrix designed for preparative chromatography. However, the design of a chromatography matrix inherently is characterized by heretofore unavoidable constraints leading to tradeoffs among objectives. For example, the requirement of a large surface area to volume ratio is critical to throughput, and practically speaking, requires the matrix to be microporous. Such microporous particulate materials are characterized by a nominal pore size which is inversely related to the surface area of the particles and a nominal particle diameter which dictates the pressure drop for a given packed column. Operations with rapid flows and small microporous particles require high operating pressures and promote bandspreading. Increasing the size of the particles decreases back pressure. Increasing the size of the pores decreases surface area and, together with increasing particle size, results in significant decreases in productivity. If rigid particles are used together with high pressures, gains in productivity can be achieved (e.g., HPLC), but plate height, the measure of bandspreading, is proportional to the flow rate of liquids through the matrix. Thus, when high surface area porous particles are used, as fluid velocity is increased, plate height increases and peak resolution decreases.

The phenomenon of bandspreading generally is described by the function:

$$H = Au^{\frac{1}{3}} + B/u + Cu \qquad \text{(Eq.-1)}$$

wherein A, B, and C are constants for a particular chromatography column, u is the velocity of fluid through the bed, and H is the plate height. The A term is a measure of bandspreading caused by longitudinal diffusion, i.e., a term accounting for the fact that there is a slow molecular diffusion along the axis of a column. The B term accounts for the fact that a fluid passing through a column can take many different paths. This is often related to as "eddy diffusion". The A and B terms dominate bandspreading phenomena in a given matrix at low fluid flow velocities. At high velocities, the contribution of these factors to bandspreading is minimal, and the phenomenon is dominated by the C term. This term accounts for stagnant mobile phase mass transfer, i.e., the slow rate of mass transfer into the pores of the particles of the matrix. As a solute front passes through a column at a given velocity, some solute will penetrate the pores and elute later than the front.

The degree of bandspreading traceable to the C term is related to particle diameter, solute diffusion coefficient inside the pores, pore size, and the velocity of the solute outside the pores. More specifically, the C term is governed by the expression:

$$H \sim Cu = \frac{cd^2 u}{D_{Eff}} \quad \text{(Eq. 2)}$$

wherein c is a constant, d is the diameter of the particle, and $D_{eff}$ is the effective diffusion coefficient of the solute within the pore. To maximize throughput, fluid velocity should be high. But as is apparent from the foregoing expression, increasing velocity increases mass transfer limitations due to pore diffusion and therefore leads to increased bandspreading and decreased dynamic loading capacity. Note also that bandspreading increases as a function of the square of the particle size. Thus, attempts to increase throughput at a given pressure drop by using higher liquid flow rates among the intersticies of large particles produces geometric increases in bandspreading caused by slow intraparticle diffusion.

It is also apparent from equation 2 that bandspreading can be reduced by increasing the effective diffusion constant. Of course, diffusion rate is an inverse function of the molecular weight of the solute and is dependent on concentration gradients. Thus, proteins having a high molecular weight typically have diffusion constants in the range of $10^{-7}$ to $10^{-8}$ cm$^2$/sec. For this reason, chromatographic separation of proteins can produce levels of bandspreading not encountered with lower molecular weight solutes. Furthermore, the effective diffusivity through the pores of the particles is lower than the diffusivity in free solution. This is because diffusion is hindered in pores having mean diameters comparable to the molecular diameter of the solute, e.g., no more than about a factor of 10 or 20 greater than the solute. Effective diffusivity differs from ideal also because the solute must diffuse into the particle from fluid passing by the particle. Increasing convective flow in what is virtually a perpendicular direction to the direction of diffusion produces an effective diffusion rate somewhat lower than the ideal.

Effective diffusivity also is decreased during loading of the surface of the sorbent with solute. This phenomenon has been explained as being due to occlusion of the entrance of the pore by adsorbed protein. As protein molecules begin to diffuse into the porous matrix, they are thought to sorb at the first sites encountered, which typically lie about the entryway of the pore. It is often the case that the dimensions of a macromolecular solute are significant relative to the diameter of the pore. Accordingly, after a few molecules have been sorbed, the entrance to the pore begins to occlude, and the passage of solute into the interior of the pore by diffusion is hindered. As a result of this occlusion phenomenon, mass transfer of solute into the interior of the sorbent particle is reduced further.

Many of the negative effects on plate height caused by stagnant mobile phase loading in porous particles may be alleviated by decreasing particle size, and therefore pore length. However, as noted above, this strategy requires operation at increased pressure drops.

Recently, it was suggested by F. E. Regnier that chromatography particles having relatively large pores may enhance performance by allowing faster diffusion of large molecules. It was thought that increasing pore size might alleviate the pore entry clogging problem and permit diffusion into the particles relatively unhindered by pore effects.

There is a different class of chromatography systems which are dominated by convective processes. This type of system comprises sorbent surfaces distributed along flow channels that run through some type of bed. The bed may be composed of non-porous particles or may be embodied as a membrane system consisting of non-porous particle aggregates, fiber mats, or solid sheets of materials defining fabricated holes. The channels of the non-porous particle systems are formed, as with the diffusion bound systems, by the interstitial space among the particles. The space between fibers forms channels in fiber mats. Channels formed by etching, laser beam cutting, or other high energy processes typically run all the way through the membrane, whereas the former type of channels are more tortuous.

In these systems, solute is carried to the sorbent surface by convective flow. Solute may be transported for relatively long distances without coming into contact with sorbent surface because channel dimensions are often quite large (0.2 to 200 μm). The flow is generally laminar, and lift forces divert solutes away from channel walls. These drawbacks to mass transfer of solute to the solid phase can be serious and present a significant obstacle to high flow rates. Thus, channels must be long to ensure that solute will not be swept through the sorbent matrix while escaping interactive contact. The provision of smaller diameter channels increases required operational pressure drops. If velocity is reduced, throughput obviously suffers. Still another disadvantage of the convective transport system is that it inherently has a relatively low surface area and accordingly less capacity than other systems of the type described above.

Elimination of the pores from a particulate sorbent can allow separations to be achieved very rapidly. For example, 2 μm non-porous particle columns can separate a mixture of seven proteins in less than fifteen seconds. However, this approach cannot solve the engineering challenges presented by the requirements for purification of high molecular weight materials as dramatically demonstrated in the table set forth below.

| CHARACTERISTICS OF NON-POROUS PARTICLE COLUMNS | | | | | | | |
| --- | --- | --- | --- | --- | --- | --- | --- |
| Particle Size (μm) | 10 | 5.0 | 2.0 | 1.0 | 0.5 | 0.1 | 0.05 |
| Surface Area (m$^2$/ml) | 0.6 | 1.0 | 3.1 | 6.3 | 10 | 63 | 105 |
| Pressure Drop (psi/cm | 17 | 68 | 425 | 1700 | 6800 | 17000 | 68000 |

| CHARACTERISTICS OF NON-POROUS PARTICLE COLUMNS |
|---|
| of bed height) |

As illustrated by these data, small particles, whether present in packed columns or membranes, have very serious pressure problems at particle sizes sufficient to provide large surface areas and large loading capacity. In contrast, 300 Å pore diameter particles in the 5 to 100 μm range have from 70 to 90 $m^2$/ml of surface area, while a 1,000 Å material has an area on the order of 40 to 60 $m^2$/ml.

A chromatography cycle comprises four distinct phases: adsorption, wash, elution, and reequilibration. The rate limiting step in each stage is the transport of molecules between the mobile fluid and the static matrix surface. Optimum efficiency is promoted by rapid, preferably instantaneous mass transfer and high fluid turnover. During sorbent loading, with a step concentration of the protein, fewer molecules are sorbed as the velocity of mobile phase in the bed increases. The consequence is that some protein will be lost in the effluent or will have been lost as "breakthrough". If the breakthrough concentration is limited to, for example, 5% of the inlet concentration, that limit sets the maximum bed velocity which the bed will tolerate. Furthermore, increases in bed velocity decrease loading per unit surface area.

As should be apparent from the foregoing analysis, constraints considered to be fundamental have mandated tradeoffs among objectives in the design of existing chromatography materials. Chromatography matrix geometry which maximizes both productivity and resolution has eluded the art.

It is an object of this invention to provide the engineering principles underlying the design of improved chromatography materials, to provide such materials, and to provide improved chromatography methods. Another object is to provide chromatography particles and matrices, derivatizable as desired, for the practice of a new mode of chromatographic separation, named herein perfusion chromatography, characterized by the achievement a high fluid flow rates but manageable pressure drops of extraordinarily high productivities and excellent peak resolution. Another object is to provide improved methods of separating and purifying high molecular weight products of interest from complex mixtures. Another object is to overcome the deficiencies of both convection bound and diffusion bound chromatography systems. Still another object is to provide a chromatography procedure and matrix geometry wherein effective plate height is substantially constant over a significant range of high fluid flow velocities, and at still higher velocities increases only modestly.

These and other objects and features of the invention will be apparent from the drawing, description, and claims which follow.

SUMMARY OF THE INVENTION

It has now been discovered that chromatography matrix geometries can be devised which, when exploited for chromatographic separations above a threshold fluid velocity, operate via a hybrid mass transport system, herein called perfusion, which couples convective and diffusive mass transport. The matrix materials are extraordinary in that they permit order of magnitude increases in productivity without significantly compromising resolution. Furthermore, surprisingly, the most dramatic improvements are achieved with relatively large particles which permit productive operation at relatively low column pressure drops. Perfusion chromatography uncouples bandspreading from fluid velocity, succeeds in achieving unprecedented combinations of throughput and resolution, and uncouples that which determines pressure drop from that which determines mass transport.

Perfusion chromatography may be used for rapid analysis and also in preparative contexts. Perhaps its optimum use is in separation and purification of large biologically active molecules such as polypeptides, proteins, polysaccharides, and the like. The technique has less advantage for small molecules with their much higher diffusion constants and inherently faster mass transport. However, even with low molecular weight materials such as sugars and alcohols, perfusion chromatography can be exploited to advantage, particularly when using large particles as a chromatography matrix material where the distance over which diffusion must act is relatively large. A use for perfusion chromatography is in separation of solutes comprising biological molecules, e.g., molecules of biological origin or having biological activity.

A key to achieving these goals is the availability of matrix materials defining at least primary and secondary sets of pores, i.e., "first" and "second" sets of interconnected pores, with the members of the first pore set having a greater mean diameter than the members of the second pore set. The matrix also defines surface regions which reversibly interact with the solutes to be separated and which are disposed in fluid communication with the members of the second pore set. The dimensions of the first and second pore sets are controlled such that when a mixture of solutes is passed through the matrix above a threshold velocity, convective flow is induced through both pore sets. The domain of perfusion chromatography begins when the rate of fluid flow increases to a level where convective flow through the members of the second pore set exceeds the rate of diffusion of the solute through those pores. At the outset, the advantages over conventional chromatography techniques are modest, but as superficial bed velocities increase, dramatic increases in productivity are achieved.

The mean diameter of the members within each of the first and second pore sets can vary significantly. In fact, one preferred matrix material comprises a second pore set having a plurality of interconnected pore subsets which permit convective flow, and smaller subpores comprising looping pores or blind pores communicating with pores where convection occurs. The subpores contribute most significantly to the surface area of the matrix. Most solute/matrix interactions occur in these subpores. Mass transfer between the surface and the members of the interconnected pore subsets occurs by way of diffusion. This type of geometry produces a second pore set with a wide distribution of mean pore diameters. In another embodiment, one or both of the first and second pore sets comprise pores having a narrow distribution of pore diameters such that the diameter of 90% of the pores in the set falls within 10% of the mean diameter of all of the pores in the set. In a preferred embodiment the subpores have a mean diameter less than about 700 Å. Preferably, the fluid mixture of solutes to be separated is passed through the matrix at a rate such that the time for solute to diffuse to and from a surface region from within one of the members of the second pore set is no greater than about ten times the time for solute to flow convectively past the region.

This type of matrix geometry has several advantages. First, in a matrix of sufficient depth, all of the liquid will pass through the second pore set numerous times, although the pressure drop is determined primarily by the larger mean diameter of the first pore set. Second, in the preferred packed particle matrix embodiment, with respect to intraparticle stagnant mobile phase constraints, the perfusive matrix behaves like a matrix of packed, non-porous particles, or porous particles of very small diameter, yet pressure and velocity requirements are characteristic of much larger particle beds. Third, mass transport between the sorbent surface and mobile phase is effected primarily by convective flow. Diffusion still must occur, but the diffusion paths are so much shorter that this constraint becomes mimimal.

In the chromatography process of the invention, the fluid mixtures, eluents, etc. preferably are passed through the matrix at a bed velocity greater than 1000 cm/hr, and preferably greater than 1500 cm/hr. Productivities exceeding 1.0 and often 2.0 mg total protein sorbed per ml of sorbent matrix per minute are routinely achieved. In the preferred packed particle matrices, the particles preferably have a mean diameter of at least about 8.0 $\mu$m, and preferably greater than 20 $\mu$m. Since, as a rule of thumb, the mean diameter of the pores defined by the intersticies among roughly spherical particles is approximately one-third the particle diameter, these interstitial pores, comprising the first pore set, will have a mean diameter on the order of about 3.0 $\mu$m, and for the larger particles, 7-20 $\mu$m or larger. The second pore set in this embodiment consists of the throughpores within the particles. Effective perfusive chromatography requires the ratio of the mean diameter of the particles to the mean diameter of the second pore sets to be less than 70, preferably less than 50. The dimensions of the first and second pore sets preferably are such that, at practical flow velocities through the bed, the ratio of the convective flow velocities through the first pore set, i.e., the intersticies among the particles, to the second pore set, i.e., the throughpores in the particles, is within the range of 10 to 100.

The chromatography matrices of the invention may take various forms including beds of packed particles, membrane-like structures, and fabricated microstructures specifically designed to embody the engineering principles disclosed herein. However, a preferred form is a packed bed of particles having a mean diameter greater than 10 $\mu$m, each of which define a plurality of throughpores having a mean diameter greater than about 2,000 Å. The particles comprise rigid solids which present a large interior solute-interactive surface area in direct fluid communication with the throughpores. Currently preferred particles comprise a plurality of interadhered polymeric spheres, herein termed "porons", which together define interstitial spaces comprising the subpores and throughpores. The subpores preferably have an average diameter in the range of 300 Å to 700Å. This approach to the fabrication of chromatography particles and matrices of the invention also permits the manufacture of particles defining branching pores, communicating between the throughpores and the subpores, which have intermediate mean diameters. Preferably, the throughpores, subpores, and any interconnecting pores are anisotropic.

In this particle fabrication technique, it is preferred to build the particles from porons to produce small poron clusters, and then to aggregate the clusters, and then possibly to agglomerate the aggregates to form particles of macroscopic size, e.g., greater than 40 $\mu$m, which optionally may themselves be interadhered to produce a one-piece matrix. This approach results in production of a second pore set comprising a plurality of throughpore subsets and subpores of differing mean diameters. Preferably, the ratio of the mean diameter of any consecutive subset of throughpores is less than 10. The ratio of the mean diameter of the smallest subset of throughpores to the mean diameter of the subpores Preferably is less than 20. The ratio of the mean diameter of the first pore set, here defined by the intersticies among the interadhered or packed particles, and the largest subset of throughpores, Preferably is less than 70, more preferably less than 50.

These and other objects and features of the inventions will be apparent from the drawing, description, and claims which follow.

BRIEF DESCRIPTION OF THE DRAWING

FIGS. 10 through 22 are graphs presenting various data demonstrating the properties of perfusion chromatography systems.

Like reference characters in the respective drawn figures indicate corresponding parts.

DESCRIPTION

Figure 1A:
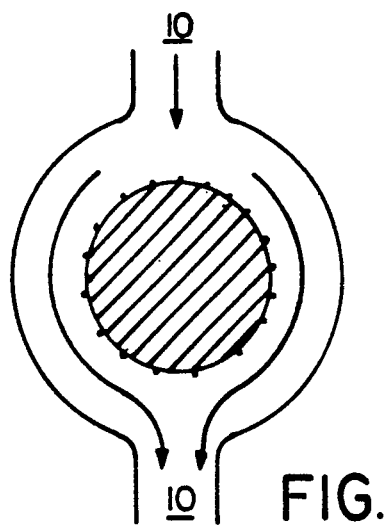
FIGS. 1A, 1B, 1C, 1D, and FIG. 2 are schematic representations of particle/matrix geometries useful in explaining perfusion chromatography.

In this specification the nature and theoretical underpinnings of the required matrix structures and operational parameters of perfusion chromatography will first be disclosed, followed by engineering principles useful in optimization and adaptation of the chromatography process to specific instances, disclosure of specific materials that are useful in the practice of perfusion chromatography, and examples of perfusion chromatography procedure using currently available materials.

Broadly, in accordance with the invention, perfusion chromatography is practiced by passing fluids at velocities above a threshold level through a specially designed matrix characterized by a geometry which is bimodal or multimodal with respect to its porosity. Perhaps the most fundamental observation relevant to the new procedure is that it is possible to avoid both the loss of capacity characteristic of convection bound systems and the high plate height and bandspreading characteristics of diffusion bound systems. This can be accomplished by forcing chromatography fluids through a matrix having a set of larger pores, such as are defined by the intersticies among a bed of particles, and which determine pressure drops and fluid flow velocities through the bed, and a set of pores of smaller diameter, e.g., anisotropic throughpores. The smaller pores permeate the individual particles and serve to deliver chromatography fluids by convection to surface regions within the particle interactive with the solutes in the chromatography fluid.

The relative dimensions of the first and second pore sets must be such that, at reasonably attainable fluid velocities through the bed, convective flow occurs not only in the larger pores but also in the smaller ones. Since fluid velocity through a pore at a given pressure is a function of the square of the pore radius, it can be appreciated that at practical fluid velocities, e.g., in the range of 400 to 4,000 cm/hr., the mean diameter of the two sets of pores must be fairly close. As a rule of thumb, the mean diameter of pores defined by the intersticies among spherical particles is about one third the diameter of the particles. Thus, for example, particles having a mean diameter of 10 $\mu$m and an average throughpore diameter of 1,000 Å, when close packed to form a chromatography bed, define first and second sets of pores having mean diameters of approximately 3 to 4 $\mu$m and 0.1 $\mu$m, respectively. Thus, the mean diameter of the larger pores is on the order of thirty to forty times that of the smaller pores. Under these circumstances, very high pressure drops are required before any significant fraction of the fluid passes by convection through the smaller pores within the particles.

Experiments with this type of material have failed to indicate perfusive enhancement to mass transport kinetics. Thus, at the flow rates tested, mass transport into the 10 $\mu$m particles appear to be dominated by diffusion. Stated differently, any convective flow within the throughpores does not contribute significantly to the rate of mass transport. Obviously, more conventional solid chromatography media such as most silica based materials, agars, dextrans and the like, which have much smaller pores (generally between approximately 50 and 300Å) and larger mean particle sizes (20 $\mu$m to 100 $\mu$m), cannot be operated practically in the perfusive mode. There simply is no realistic flow velocity attainable in a practical system which results in any significant convective flow within their secondary micropores. Generally, larger mean diameter throughpores, or more specifically, a smaller mean diameter ratio between the first and second pore sets, is required to practice perfusion chromatography.

The nature of perfusion chromatography and its required matrix geometry may be understood better by reference to FIGS. 1A through 1D. These are schematic diagrams roughly modeling the fluid flow in various types of chromatography matrices showing in schematic cross section one region of the matrix. The chromatography particle or region is accessed by a major channel 10 on the "north" side which leaves from the "south" side and may or may not have a circumventing channel which allows the fluid mobile phase containing dissolved solutes to by-pass the particle. The particles themselves comprise a plurality of solute interactive surface regions represented by dots which must be accessed by solute molecules. The nature of these regions depends on the chemistry of the active surface. The process of this invention is independent of the nature of the active regions which, in various specific embodiments, may take the form of surfaces suitable for cationic or anionic exchange, hydrophobic/hydrophilic interaction, chelation, affinity chromatography, hydrogen bonding, etc. Low plate height and minimization of bandspreading require rapid mass transfer between the interactive surface regions and the fluid mobile phase. High capacity requires both rapid mass transfer and the presence of a large number of interactive regions, i.e., high surface area. Solute is transported by two mechanisms: convection, which is determined by pore size, pressure drop, pore-length and tortuosity and local geometry about the entry and exit of the pore; and intrapore diffusion, which is a function primarily of the molecular dimensions of the various solutes, the dimensions of the pore, and of concentration gradients.

Figure 1C:
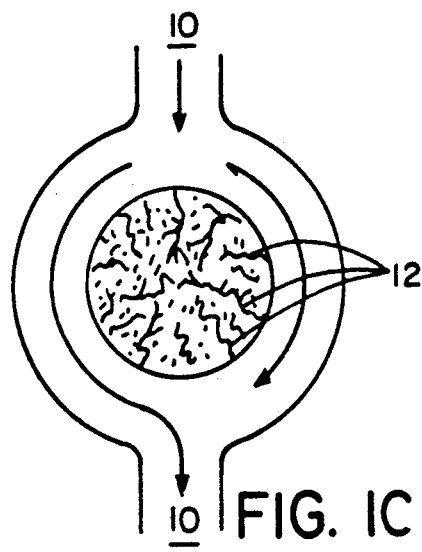
Figure 1B:
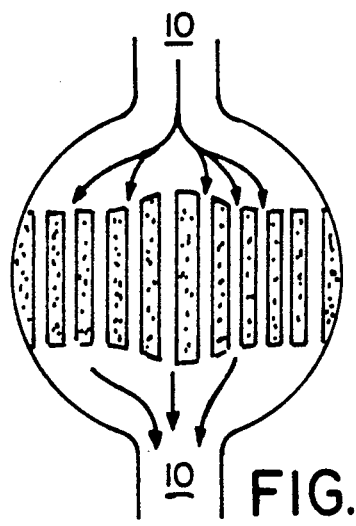
Figure 1D:
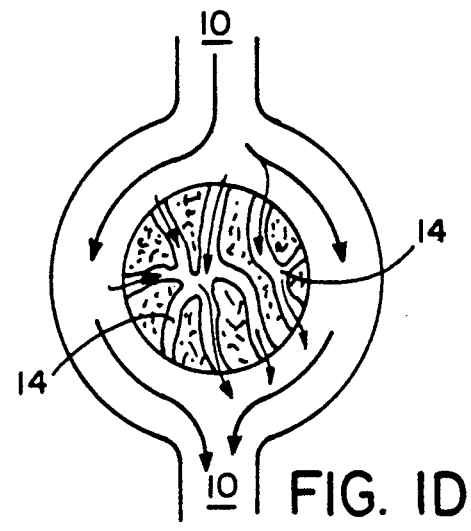

The mechanism of solute interaction with the matrix in two types of convection bound chromatography systems will be disclosed with reference to FIGS. 1A and 1B; diffusive bound systems with reference to FIG. 1C; and perfusive systems with reference to FIG. 1D.

FIG. 1A represents the chromatography matrix comprising close packed non-porous particles. The interior of the particles is barred to access by solute molecules. The only interactive surface elements that are available to the solute molecules are those arrayed about the exterior surface of the particle. FIG. 1B represents a membrane-like chromatography "particle" (actually a region in a solid matrix) having throughpores and interactive surface regions disposed along the walls. The geometry of FIG. 1B is analogous to filter beds and polymer web morphologies (e.g., paper and membrane filters) and to bundles of non-porous fibers or tubes. In the morphologies of FIGS. 1A and 1B, only the outside surface of the chromatography mandrel contributes to the capacity of the matrix. The surface area to volume ratio of these geometries is relatively low, and they are therefore inherently low productivity systems. Provided the flow paths 10 are long enough, very rapid separations and high resolution without breakthrough can be achieved because the distance a solute molecule must diffuse from a convective channel to an interactive surface element is small. Of course, an attempt to increase the number of interactive surface elements (surface area) by decreasing particle size (FIG. 1A) or decreasing pore diameter (FIG. 1B) amounts to a tradeoff for higher operating pressure. Increasing the fluid velocity through the bed beyond the optimal degrades performance.

In FIG. 1C, the interactive surface elements are disposed about the interior of the particle and, per unit volume of particle, are far more numerous. Here, the interior of the matrix is accessible via small pores 12. Solute can pass through these pores only by diffusion, or by a combination of diffusion coupled with an extremely slow convection which has no significant effect on the overall kinetics of mass transport. Accordingly, solute molecules are moved from flow channel 10 into the interior of the particle by slow diffusive processes. This constraint can be alleviated by making the particles smaller and therefore decreasing the distance required to be traversed by diffusion. However, again, this is achieved at the expense of greatly increasing required operational pressure drops. For macromolecules such as proteins, the effective diffusivity within the pores is decreased further by the pore surface hindrance and occlusive effects as discussed above.

When such porous particles are fully loaded, i.e., solute molecules have diffused along the pores and are now occupying all interactive surface regions, the matrix is washed, and then elution commences. These sudden changes in conditions induce solutes to evacuate the particles. This, again, is accomplished by slow diffusion. Gradually, solute from the center of the particle arrives at the ring channel to be carried off by convection. This delay in "emptying" the particle by diffusion is a contributing cause of the trailing tail on a chromatography pulse which reduces resolution. The rate at which the particle can be loaded and unloaded determines the kinetics of the chromatography process. Clearly, the faster solute can escape, the shorter the time for all of the solute to arrive at the chromatography column's output, and hence the shorter the straggling tail and the less bandspreading. Increasing fluid velocity in channels 10 above an optimal level has no positive effect on throughput and causes plate height to increase and resolution to decrease.

FIG. 1D models a matrix particle suitable for perfusion chromatography. As illustrated, in addition to channels 10 having a relatively large mean diameter (defined by the intersticies among particles in the particulate matrix embodiment) the matrix also comprises a second set of pores 14, here embodied as throughpores defined by the body of the particle. The mean diameter of the pores 14 is much larger than the diffusive transport pores 12 of the conventional chromatography particle depicted in FIG. 1C. The ratio of the mean diameters of pores 10 and 14 is such that there exists a fluid velocity threshold which can practically be achieved in a chromatography system and which induces a convective flow within pores 14 faster than the diffusion rate through pores 14. Precisely where this threshold of perfusion occurs depends on many factors, but is primarily dependent on the ratio of the mean diameters of the first and second pore sets, here pores 10 and 14, respectively. The larger that ratio, the higher the velocity threshold.

Actually, the bed velocity corresponding to the threshold is that at which intraparticle convection begins to influence transport kinetics. At much higher velocities convection dominates and significant performance improvements are observed.

In matrices comprising close packed 10 μm particles, tne mean diameter of pores 10 (comprising the intersticies among the particles) is on the order of 3 μm. Such 10 μm particles having throughpores of about 1,000 Å in diameter (0.1 μm) do not perfuse at practical flow rates; 10 μm particles having a plurality of pores within the range of 2000 Å to 10,000 Å (0.2 mm-1.0 μm) perfuse well within a range of high fluid velocities through the bed (approx. 1000 cm/hr or greater). In matrices comprising closepacked particles having 1,000 Å mean diameter throughpores, the ratio of the mean diameter of the first to the second pore set is about 3.3/0.1 or approximately 33. For the corresponding 4,000Å mean diameter throughpore particle, the ratio is approximately 8.3. While these numbers are rough and are dependent on many assumptions, the ratio of the mean diameters of the first and second pore sets effective to permit exploitation of the perfusion chromatography domain with operationally practical flow rates is believed to lie somewhere within this range, i.e., 8-33.

Again referring to FIG. 1D, it should be noted that mass transport to regions within the particle and into the vicinity of the interactive surface elements is dominated by convection. While diffusive mass transport is still required to move solutes to and from pores 14 and the interactive surface regions, the distance over which diffusive transport must occur is very significantly diminished. Thus, with respect to bandspreading and mass transfer kinetics, the bed behaves as if it were comprised of very fine particles of a diameter equal approximately to the mean distance between adjacent throughpores (e.g., on the order of 1.0 μm with currently available materials). It has a high surface area to volume ratio and rapid kinetics. However, operating pressure drop essentially is uncoupled from these properties as it is determined by the larger dimensions of channels 10 comprising the first pore set.

At low velocities through the matrix, perfusive particles such as the particles schematically depicted in FIG. 1D behave similarly to diffusion bound conventional chromatography materials. At low velocities, convective flow essentially is limited to the larger first set of pores 10. Convective flow within pores 14 is so small as to be negligible, transport from within the particle to the flow channels 10 takes place through diffusion. The larger pores permit more optimal diffusion rates as occlusive effects and diffusion hindrance within pores are somewhat alleviated.

As the fluid velocity in the bed (and pressure drop) is increased, there comes a point when the convective flow rate through the pores 14 exceeds the rate of diffusion and operation in the perfusive mode commences. This flow rate is about 300 cm/hr for 10 μm chromatography particles having 4,000 Å pores for a solute having a pore diffusivity of $10^{-7}$ cm$^2$/sec. Above this threshold, it will be found that increased pressure drop and velocity permit increased throughput per unit volume of matrix never before achieved in chromatography systems. At about 600 cm/hr productivities approximately equal to the highest heretofore achieved are observed. At 1000 cm/hr to 4000 cm/hr, extraordinary productivities are achieved. Furthermore, these productivities are achieved without the expected increase in bandspreading, i.e., decrease in resolution.

While this behavior seemingly violates long established physical principles governing the general behavior of chromatography systems, recall that at high velocities the primary contributor to bandspreading is stagnant mobile phase mass transfer within the particle, or the "C term" discussed above. Thus, in the perfusive system:

$$H \sim Cu = \frac{cd^2 u}{D_{Eff}} \quad \text{(Eq. 2)}$$

However, $D_{Eff}$ which, at low fluid velocities through the matrix, is a measure of the effective diffusion of solute into the pores 14 and into contact with the surface regions, becomes, in the perfusive mode, a convection dominated term. In general, one can approximate $D_{Eff}$ as the sum of a diffusive element (pore diffusivity) and a convective element (pore velocity x particle diameter). Calculated in this way $D_{Eff}$ is a conservative estimate which ignores the different driving forces for the two modes of transport. For any given fluid velocity and bed geometry operated in the perfusive mode, the ratio of fluid velocity within the second pore set to superficial fluid velocity in the bed will be given by:

$$\frac{V_{pore}}{V_{bed}} = \alpha \quad \text{(eq. 3)}$$

wherein $\alpha$ is a constant. Thus, fluid velocity within the members of the second pore set becomes $\alpha V_{bed}$, and the plate height due to the C term effectively becomes:

$$H \sim Cu = \frac{cd\,u}{\alpha V_{bed}} \quad \text{(Eq. 4)}$$

Since u represents the velocity of fluid in the bed, the plate height reduces to:

$$H = c'd \quad \text{(Eq. 5)}$$

Thus, the C term becomes substantially independent of bed velocity in the perfusion mode. It will not be completely independent because, as noted above, diffusion still will play a part in mass transfer between convective channels and sorptive surface regions. At some high $V_{Bed}$, the system will once again become kinetically bound by mass transfer resistance due to diffusion into subpores.

One measure of the mass transfer of a solute through a pore is given by a characteristic Peclet number ($P_e$), a dimensionless quantity equal to VL/D, where V is the convective velocity through the pore, L is its length, and D is the diffusivity of the solute through the pore. In the prior art systems, under all regimes, the Peclet number which describes the ratio of convective to diffusive transport within the pores of a chromatography material was always much less than one. In perfusive chromatography, the Peclet number in the second set of pores is always greater than one.

Figure 2:
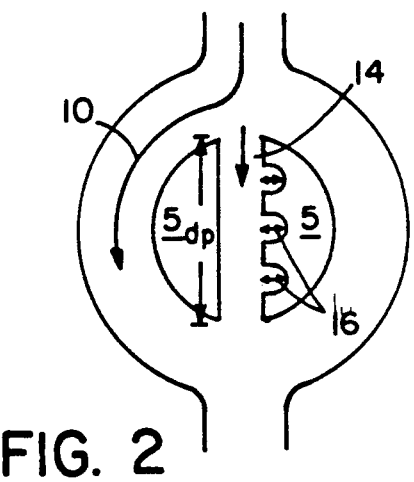

Referring to FIG. 2, a conceptual model of a region of matrix 5 depicted in cross-section has three types of pores; the members of the first pore set 10; throughpores 14 comprising the members of the second pore set; and subpores 16. These, respectively, are characterized by Peclet numbers $P_e I$, $P_e II$, and $P_e III$, given below:

$$P_e I = \frac{V_{bed} d_p}{\epsilon D_{Eff}} \quad \text{(Eq. 6)}$$

$$P_e II = \frac{V_{pore} d_p}{D_1} \quad \text{(Eq. 7)}$$

$$P_e II = \frac{V_{pore} L_d}{D_2} \quad \text{(Eq. 8)}$$

wherein Epsilon is the void volume of the bed, $d_p$ is the diameter of the particle (representitive channel length average over a particle, includes a correction for tortuosity), $L_d$ is the depth of the sub pore, $D_{EFF}$ is the effective diffusivity within the throughpore, $D_1$ is the restricted diffusivity in the throughpores, and $D_2$ is the restricted diffusivity in the subpores.

The kinetics of chromatography in general is adversely affected by high $P_e I$, low $P_e II$, and high $P_e III$. Thus, chromatographic performance is enhanced if effective diffusivity increases, or if particle size decreases or $V_{Bed}$ decreases. At high $P_e I$, high convection rates sweep the solute past the throughpores, thus discouraging mass transfer. On the other hand, in the second pore set a high Peclet number is preferred. When $P_e II$ is high, mass transfer increases as the convective velocity takes over from diffusion as the dominant mechanism in mass transport through a particle. Within subpore 16, a low Peclet number is desired. When $P_e III$ is low, diffusion to the active surface within the sub pores is faster than flow through the particle, and consequently dynamic capacity remains high.

Increasing mobile phase velocity deteriorates the performance of diffusive systems, but has far less effect with perfusion. Instead, an increase in bed velocity yields a corresponding increase in pore velocity which controls the mass transfer kinetics inside the support. Thus, with the correct geometric relationship of the matrix, proper flow rates, pressure drops, and fluid viscosities, a domain is obtained where the mass transport characteristics of the system favor simultaneously very high throughput and high resolution separations.

Figure 3:
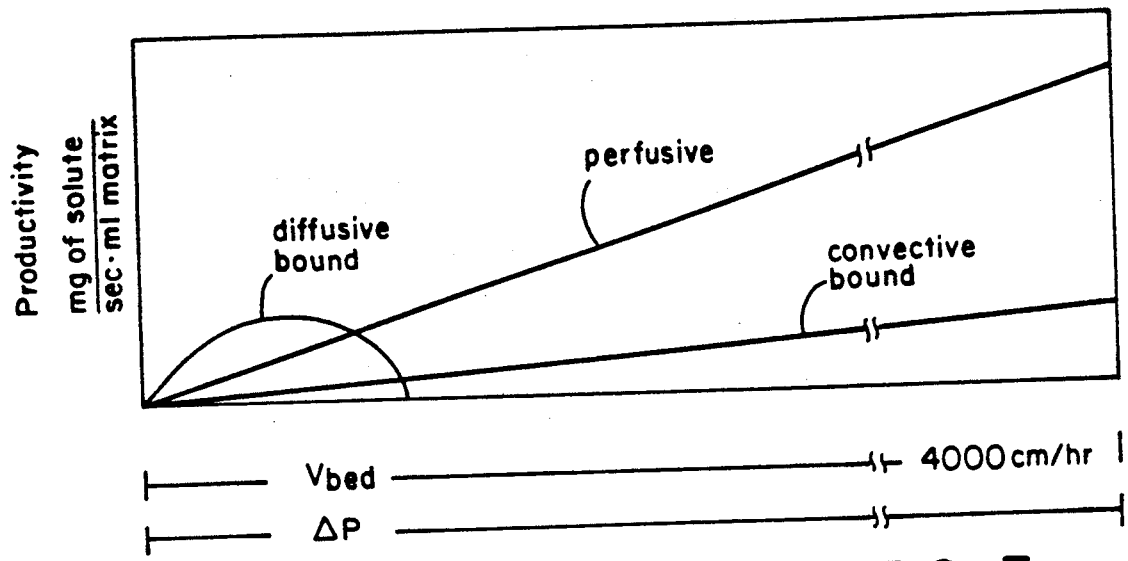
FIG. 3 is a graph of productivity versus fluid velocity ($V_{Bed}$) and operational pressures ($\Delta P$) illustrating the domains of diffusively bound, convectively bound, and perfusive chromatography systems.

FIG. 3 is a graph of productivity in milligrams of solute per second per ml of matrix versus bed velocity and pressure drops. The graph illustrates the difference in behaviors among diffusively bound chromatography systems, convectively bound systems, and perfusive systems. As shown, in conventional diffusion limited system as velocity and pressure are increased productivity increases until a maximum is reached, and further increases in $V_{Bed}$ result in losses in productivity, typically resulting in breakthrough or loss in dynamic loading capacity well prior to a bed velocity of about 400 cm/hr. In convectively bound systems, much higher fluid velocities and pressure drops may be used. For a bed of sufficient length, productivity will increase steadily, possibly up to as high as 4,000 cm/hr fluid flow rate, but the gains in productivity are modest due to the inherently low surface area and binding capacity. For perfusion systems, increases in bed velocity at the outset increase productivity in a manner similar to diffusively bound systems. However, above a threshold bed velocity, when the Peclet number in the throughpores becomes greater than 1, or convective flow velocity exceeds diffusive flow velocity within the pores, the perfusive realm is entered. Further increases in velocity serve to increase convection within the pores and increase mass transport. At some high flow rate, the perfusive system becomes diffusively bound because the time it takes for a solute molecule to diffuse to and from a throughpore to an interactive surface region becomes much greater than the time it takes a solute molecule to move by convection on past the region. However, the distance over which diffusion must act as the transport mechanism is much smaller than in conventional diffusion bound systems. Thus, optimal perfusive performance continues at least through the bed velocity where the subpore diffusion time is ten times as great as the throughpore convective time.

To evaluate the implications of perfusive kinetics on chromatography bed sorption, existing models were modified and used to simulate the sorption process. Column sorption behavior often is shown in the form of solute "breakthrough" curves which comprise a plot of effluent concentration vs. time. For a given column, if the flow rate of the feed to the sorptive surface is sufficiently slow to permit the contact time between the solute and the sorbent to be long enough to overcome finite mass transfer rates, equilibrium sorption is achieved. In this case, the initial amount of solute loaded onto the column is sorbed and no solute appears in the column effluent. When sufficient solute is loaded onto the column to saturate the sorbent phase, no more solute can be sorbed and the solute concentration in the effluent matches that of the feed. In practice, in diffusively bound systems, sorption deviates from the equilibrium limit due to slow mass transport rates.

Figure 6:
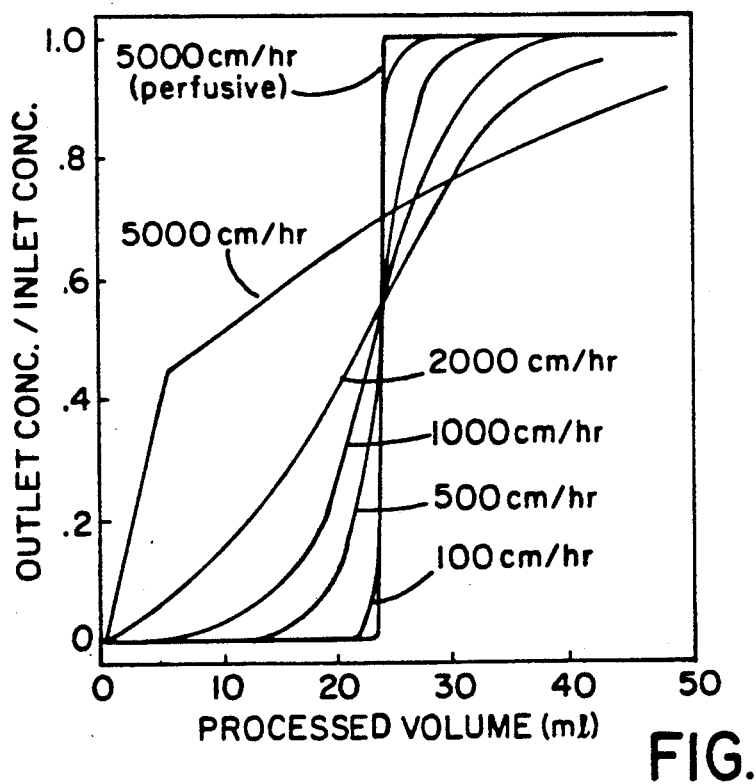
FIG. 6 is a solute breakthrough curve of outlet concentration/inlet concentration vs process volume in milliliters illustrative of the differences in kinetic bahavior between conventional and perfusion chromatography.

FIG. 6 is a graph of breakthrough (outlet concentration/inlet concentration) vs. processed volume illustrating a fundamental difference between conventional diffusive bound and perfusive chromatography systems. The curves were calculated assuming a feed protein concentration of 5 mg/ml, 3.25 mls of sorbent, a column 5.4 cm long and 1.1 cm wide, a column void fraction of 0.35, an available surface area of 40 mg/ml of matrix, and a sorption constant of 1 ml/mg. As illustrated in FIG. 6, in conventional chromatography procedures, increasing the bed velocity has the effect of skewing the curve from the ideal. At 100 cm/hr, the breakthrough curve is almost completely vertical because solute/sorbent equilibrium is established. As linear bed velocity increases, mass transfer rates begin to dominate and premature solute breakthrough occurs. Compare, for example, the curves for 500, 1,000, and 2000 cm/hr. At very high bed velocities, e.g., 5,000 cm/hr, premature solute breakthrough is severe, because a fraction of the feed solute passes through the column without being sorbed, as shown by the immediate jump in effluent solute concentration.

In contrast, for a similar column having the same simulation condition wherein the matrix is perfusive, the predictive solute breakthrough curve is much sharper and is similar to the equilibrium sorption limit. This predicted behavior was verified by experiment, as is discussed below.

Figure 7:
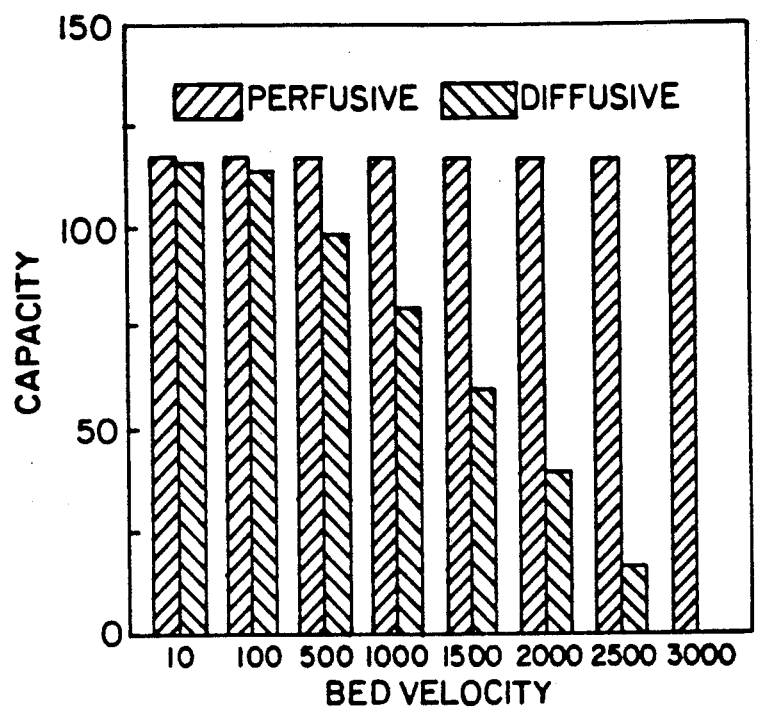
FIG. 7 is a bar graph of capacity in mgs for a bed of a given volume vs. superficial fluid flow velocity through the bed comparing the adsorption capacity of a typical perfusive column with a conventional diffusive column.

In preparative chromatography, frontal column loading typically is terminated at the point where solute effluent concentration reaches 10% of the feed concentration. The amount of feed processed until that point defines the column capacity. This capacity term is an important determinant to overall productivity in the system, and typically decreases as the bed velocity increases in a diffusive particle column. Thus, at high bed velocities, for example, in excess of 2500 cm/hr, the initial solute breakthrough is in excess of 10% of the feed, and thus column capacity is effectively zero. In contrast, as shown in FIG. 7, the capacity of a perfusive particle column remains substantially constant over a significant range of flow rates, since sorption kinetics are fast, and consequently, premature solute breakthrough occurs only at much higher levels.

PERFUSIVE MATRIX ENGINEERING

From the foregoing description many of the basic engineering goals to be pursued in the fabrication of matrix materials suitable for the practice of perfusion chromatography will be apparent to those skilled in the art. Thus, what is needed to practice perfusion chromatography is a matrix which will not crush under pressure having a bimodal or preferably multimodal pore structure and as large a surface area per unit volume as possible. The first and second pore sets which give the material its bimodal flow properties must have mean diameters relative to each other so as to permit convective flow through both sets of pores at high $V_{beds}$. The provision of subpores in the matrix is not required to conduct perfusion chromatography but is preferred because of the inherent increase in surface area per unit volume of matrix material such a construction provides.

The matrix can take the form of a porous, one-piece solid of various aspect ratios (height to cross-sectional area). Cross-sectional areas may be varied from a few millimeters to several decimeters; matrix depth can vary similarly, although for high fluid flow rates, a depth of at least 5 mm is recommended to prevent premature breakthrough and what is known as the "split peak" phenomenon. The structure of the matrix may comprise a rigid, inert material which subsequently is derivatized to provide the interactive surface regions using chemistries known to those skilled in the art. Alternatively, the structure may be made of an organic or inorganic material which itself has a suitable solute interactive surface. Methods of fabricating suitable matrices include the construction of particles which are simply packed into a column. These optionally may be treated in ways known in the art to provide a bond between adjacent particles in contact. Suitable matrices also may be fabricated by producing fiber mats containing porous particles which provide the chromatography surface. These may be stacked or otherwise arranged as desired such that the intersticies among the fibers comprise the first pore set and the throughpores in the particles the second pore set. Matrices also may be fabricated using laser drilling techniques, solvent leaching, phase inversion, and the like to produce, for example, a multiplicity of anisotropic, fine pores and larger pores in, for example, sheet-like materials or particulates which are stacked or aggregated together to produce a chromatography bed.

The currently preferred method for fabricating the matrices of the invention involves the buildup of particles preferably having a diameter within the range of 5 $\mu$m to 100 $\mu$m from much smaller "building block" particles, herein referred to as "porons", produced using conventional suspension, emulsion, or hybrid polymerization techniques. Preferably, after fabrication of the particles, the interactive surface regions are created by treating the high surface area particles with chemistries to impart, for example, a hydrophilic surface having covalently attached reactive groups suitable for attachment of immunoglobulins for affinity chromatography, anionic groups such as sulfonates or carboxyl groups, cationic groups such as amines or imines, quaternary ammonium salts and the like, various hydrocarbons, and other moities known to be useful in conventional chromatography media.

Methods are known for producing particles of a given size and given porosity from porons ranging in diameter from 10 nm to 1.0 $\mu$m. The particles are fabricated from polymers such as, for example, styrene cross-linked with divinylbenzene, or various related copolymers including such materials as p-bromostyrene, p-styryldiphenylphosphine, p-amino sytrene, vinyl chlorides, and various acrylates and methacrylates, preferably designed to be heavily cross-linked and derivatizable, e.g., copolymerized with a glycidyl moiety or ethylenedimethacrylate.

Generally, many of the techniques developed for production of synthetic catalytic material may be adapted for use in making perfusion chromatography matrix particles. For procedures in the construction of particles having a selected mean diameter and a selected porosity see, for example, Pore Structure of Macroreticular Ion Exchange Resins, Kunin, Rohm and Haas Co.; Kun et al, the Pore Structure of Macroreticular Ion Exchange Resins; J. Polymer Sci. Part C, No. 16, pgs. 1457-1469 (1967); Macroreticular Resins III: Formation of Macroreticular Styrene-Divinylbenzene Copolymers, J. Polymer Sci., Part A1, Vol. 6, Pgs. 2689-2701 (1968); and U.S. Pat. No. 4,186,120 to Ugelstad, issued Jan. 29, 1980. These, and other technologies known to those skilled in the art, disclose the conditions of emulsion and suspension polymerization, or the hybrid technique disclosed in a Ugelstad patent, which permit the production of substantially spherical porons by polymerization. These uniform particles, of a predetermined size on the order of a few to a few hundred angstroms in diameter, are interadhered to produce a composite larger particle of desired average dimension comprising a large number of anisotropic throughpores, blindpores, and various smaller throughpores well suited for the practice of perfusion chromatography. The difference between the chromatography particles heretofore produced using these prior art techniques and particles useful in the practice of this invention lies in the size of the throughpores required for perfusion chromatography.

One source of particles suitable for the practice for perfusion chromatography is POLYMER LABORATORIES (PL) of Shropshire, England. PL sells a line of chromatography media comprising porons of polystyrene cross-linked with divinylbenzene which are agglomerated randomly during polymerization to form the particles. PL produced and subsequently marketed two "macroporous" chromatography media comprising particles having an average diameter of 8 $\mu$m to 10 $\mu$m and a particle-mean pore diameter of 1000 Å and 4,000 Å. Actually, the mean pore diameter of the particles represents an average between throughpores and subpores and thus bears little significance to the perfusion properties of these materials. The inventors named herein discovered that these particles have mean throughpore diameters exceeding 2000 Å in the case of the "1000 Å" particle, and 6000 Å in the case of the "4000 Å" particle. These types of particle geometries can be made to perfuse under appropriate high flow rate conditions disclosed herein.

One type of PL particle, said to be useful for reverse phase chromatography, is an untreated polystyrene divinylbenzene (PSDVB). Its interactive surfaces are hydrophobic polymer surfaces which interact with the hydrophobic patches on proteins. A second type of particle has interactive surface elements derivatized with polyethyleneimine and act as a cationic surface useful for anionic exchange. Both types of particles were produced in an ongoing effort initiated by F. E. Regnier to increase intraparticle diffusion of large solutes such as proteins by increasing pore size. These particles were used by the inventors named herein in the initial discoveries of the perfusive chromatography domain.

These materials are sold under the tradenames PLSAX 4000 for the polyethyleneimine derivatized material and PLRP-S 4000 for the underivatized material. While they are by no means optimal for perfusion chromatography, the pores defined by the intraparticle space in a packed bed of these materials and the throughpores in the particles have an appropriate ratio for achieving perfusion chromatography under practical flow conditions.

Figure 4D:
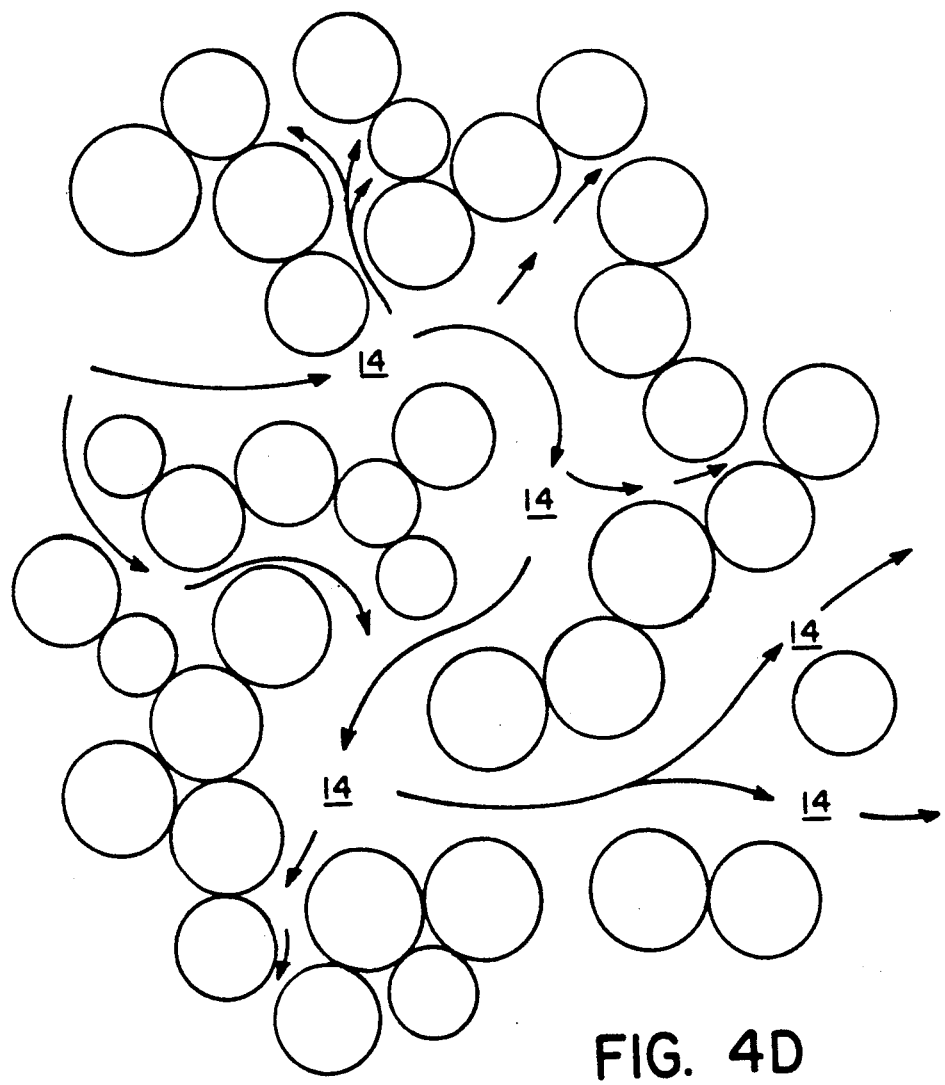
FIG. 4D is a schematic diagram illustrating the fluid dynamics which are believed to be controlling during perfusion chromatography using the particle structure shown in FIG. 4A-4C.
Figure 4A:
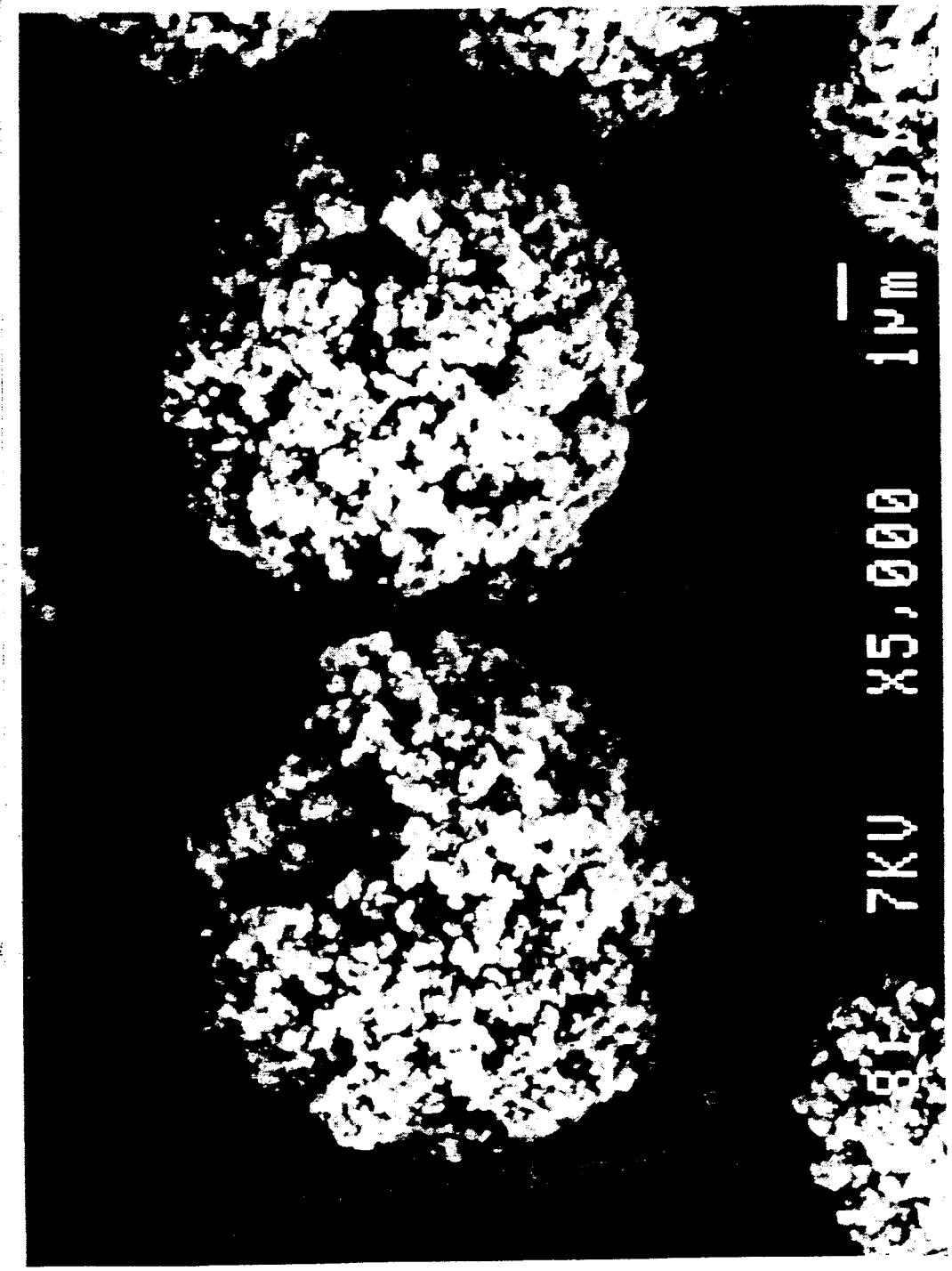
FIG. 4A, 4B, and 4C are scanning electron micrographs of a macroporous chromatography particle useful for fabricating matrices for the practice of perfusion chromatography: 4A is 10,000×; 4B is 20,000×, and 4C is 50,000×.
Figure 4B:
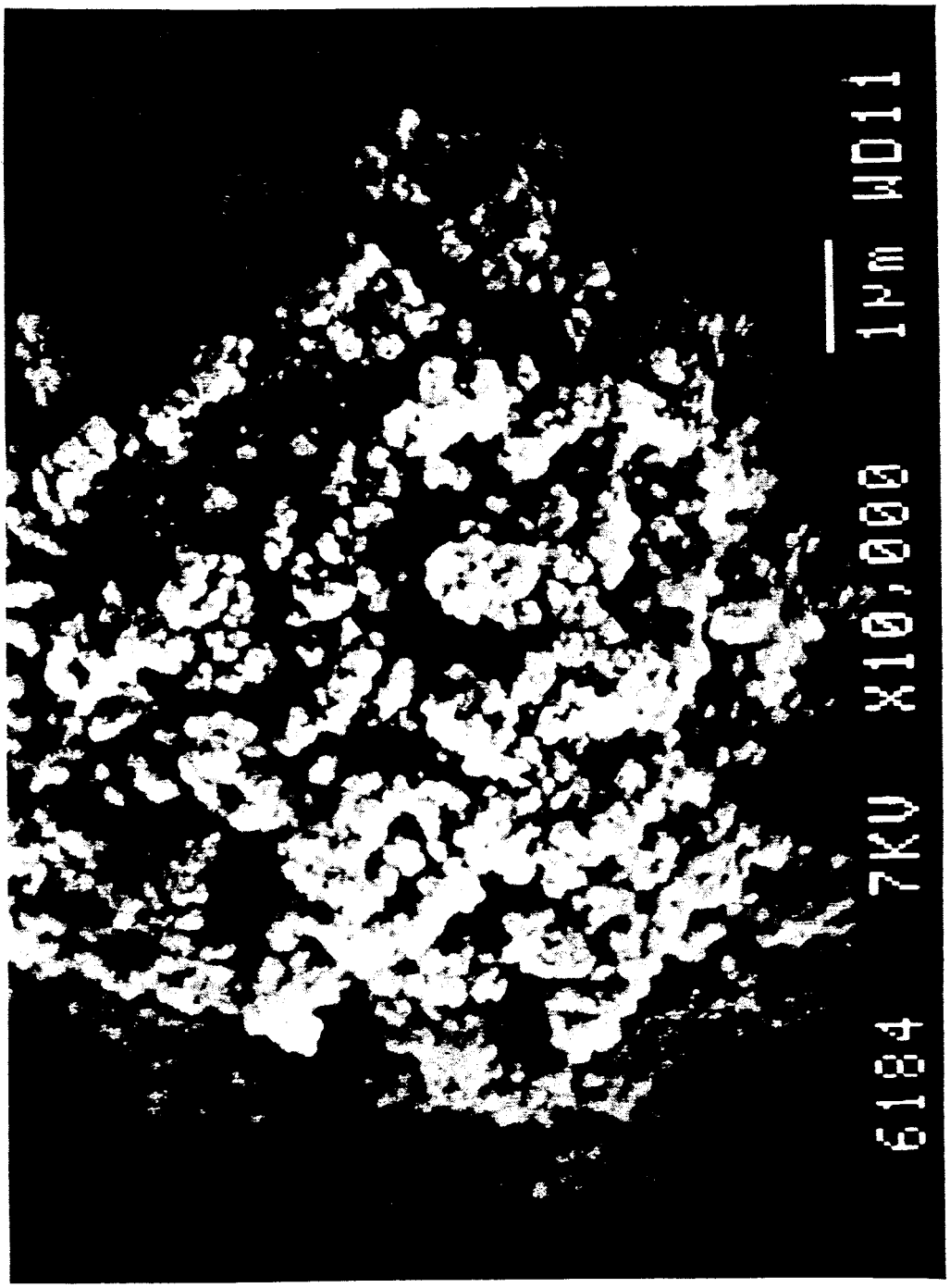
Figure 4C:
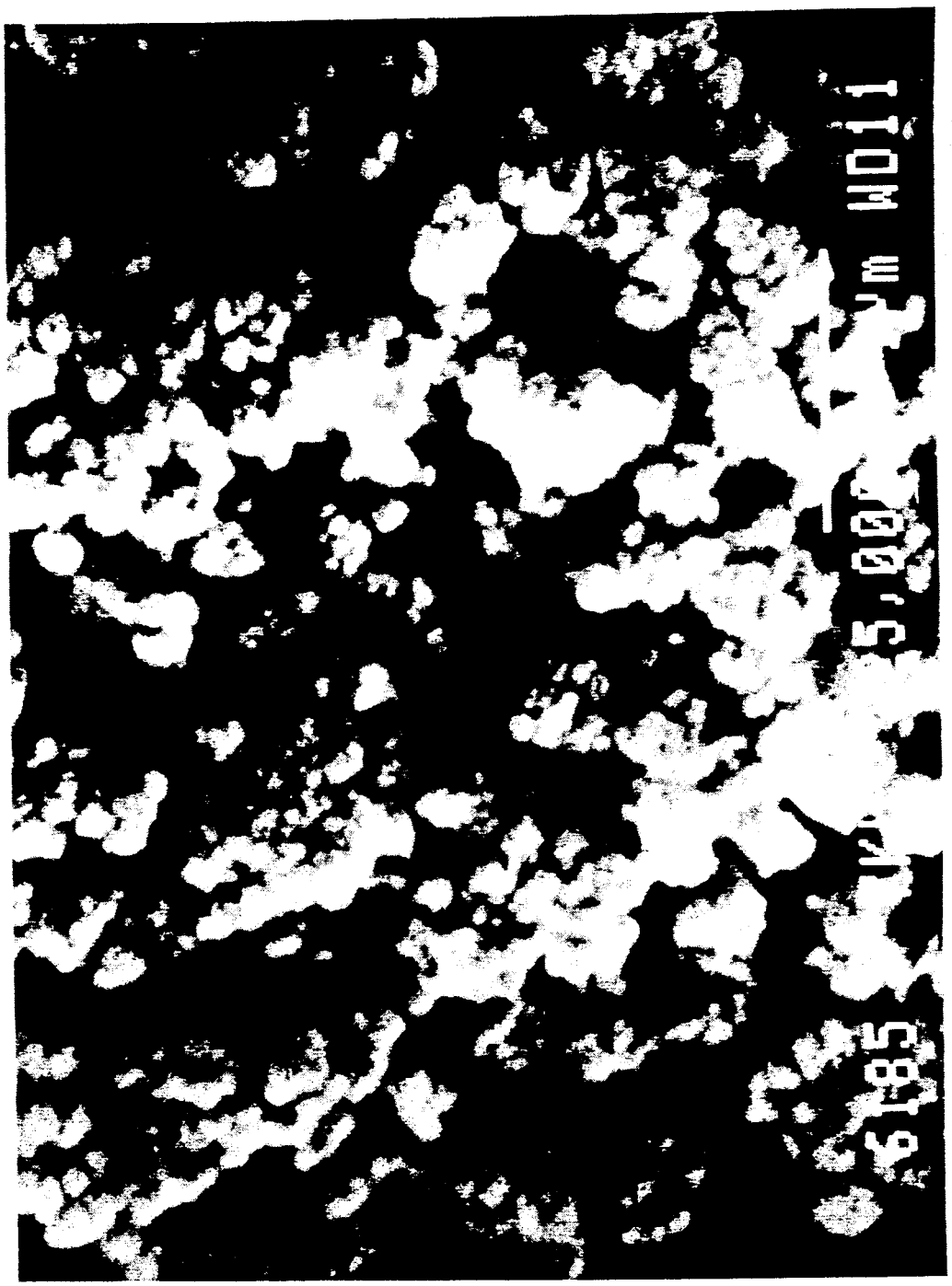

Referring to FIGS. 4A, 4B, and 4C scanning electron micrographs of PL's 10 $\mu$, 4,000 Å porous particle are shown. As illustrated in FIG. 4C, the material comprises a multiplicity of interadhered porons, approximately 1500 Å-2000 Å in diameter, which appear to be agglomerated at random to produce an irregular high surface area, and a plurality of throughpores and subpores.

As shown in FIG. 4D, at a suitable $V_{bed}$, chromatography fluids move by convection through tortuous paths within the particle. The perfusive pores are anisotropic, branch at random, vary in diameter at any given point, and lead to a large number of blind pores in which mass transport is dominated by diffusion. The blindpores and looping pores (subpores) generally have a mean diameter considerably smaller than the diameter of the porons (on the order of $\frac{1}{3}$), and a depth which can vary from as little as a fraction of the diameter of the porons to 5 to 10 times the diameter of the porons.

Figure 5C:
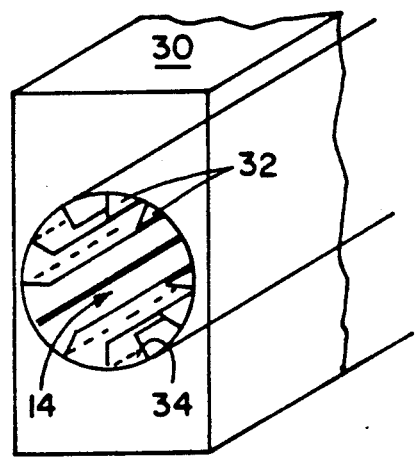
FIG. 5C is a schematic diagram illustrating one idealized structure for a perfusion chromatography matrix element.
Figure 5A:
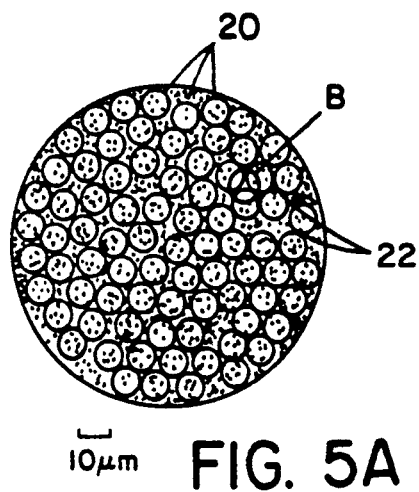
FIG. 5A is a schematic cross-section of a chromatography column.
Figure 5B:
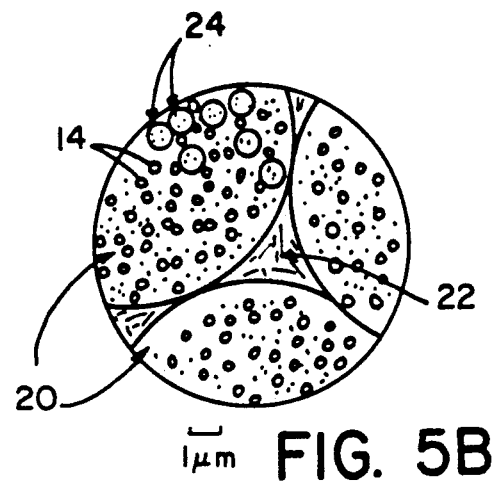
FIG. 5B is a schematic detail of the circle B shown in FIG. 5A.

FIGS. 5A and 5B illustrate scale factors of the geometry schematically. FIG. 5A is a cross section of a chromatography column showing a multiplicity of particle 20 each of which contacts its neighbors and define intersticies 22 which, in this form of matrix embodying the invention, comprise the first pore set. As illustrated, the particles are approximately 10 micrometers in diameter. The mean diameter of the intersticies vary widely but generally will be on the order of $\frac{1}{3}$ of the mean diameter of the particles 20. Circle B in FIG. 5A is exploded tenfold in FIG. 5B. Here, the microstructure of the bed on a scale of approximately 1 micrometer is illustrated. The particles comprise clusters of porons illustrated as blank circles 24. The intersticies among the poron clusters define throughpores 14. The individual porons making up clusters 24 here are illustrated by dots. At the next level of detail, i.e., 0.1 $\mu$m, or 1000 Å (not shown), a poron cluster 24 would be seen to comprise a roughly spherical aggregation of porons. In such a structure, the intersticies among the porons making up the aggregates 24 are analagous to the diffusively bound particle of conventional chromatography media such as is schematically depicted in FIG. 1C. Only in these would mass transport be diffusion dependent.

It may be appreciated that the chromatography matrices of the type described above made from aggregations of smaller particles exhibit a self similarity over several geometric length scale and are thus "fractals" in the nomenclature of Mandlebrot.

The ideal perfusive chromatography matrix for preparative separation of a given protein would comprise subpores dimensioned to permit diffusive transport. Thus, the intersticies among the porons should be larger for higher molecular weight proteins. This requires that larger porons be agglomerated. Fortunately, known polymerization techniques exploiting micelle, emulsion, suspension, and "swollen emulsion" polymerization, and various techniques involving homogenization of immiscible mixtures are known. These techniques enable preparation of variously sized particles, as disclosed, for example in the references noted above and in *Uniform Latex Particle*, (Bangs, L. B., Seradyn, Inc 1987). These methods can be used to make particles of uniform mean diameter ranging from 200 Å up to about 20 μm. For the PL 1,000 and 4,000 materials discussed above, the clusters 24 are, respectively, on the order of 1 μm and 2 μm.

In contrast to the PL 4,000 material, which, with respect to its pore structure, is multimodal, a more ideal perfusive particle might comprise a plurality of sets of throughpores and subpores of differing mean diameters. A bimodal pore size distribution can be achieved in such particle by mixing equal ratios of particles having two discrete pore sizes or by engineering this feature at the polymerization stage. Ideally, mean diameter ratio between throughpore subsets would be less than 10, the mean diameter ratio between the smallest throughpore sets and the subpores would be less than 20, and the mean diameter ratio between the first pore set, i.e., the intersticies among the particles making up the matrix, and the largest throughpore subset would be less than 70, and preferably less than 50. A multimodal material might be produced by agglomerating 500 Å porons to form approximately 1 μm clusters, which in turn are agglomerated to form 10 μm aggregates, which in turn may be aggregated to form 100 μm particles. In such a design, the 1 μm clusters would have intersticies of a mean diameter in the vicinity of a few hundred Å. These would define the subpores and provide a very high surface area. Diffusive transport within these pores would rarely have to exceed a distance of 0.5 μm or 5,000 Å. Intersticies among the 1 μm clusters making up the 10 μm aggregates would permit convective flow to feed the diffusive pores. These would be on the order of 0.3 μm in diameter. These throughpores, in turn would be fed by larger pores defined by intersticies among the 10 μm particles making up the 100 μm particles. These would have a mean diameter on the order of 35 μm.

From the foregoing it should be appreciated that the discussion regarding first and second pore sets and their relative dimensions is an idealization which, although achievable in practice, is not necessarily optimal. However, this idealization is useful in understanding the nature and properties of perfusion chromatography systems. In practice, both pore sets can vary widely in average diameter, particularly the second pore set.

Referring to FIG. 5C, a different form of perfusive chromatography media is illustrated as an impervious material 30 comprising a prefabricated throughpore 14. As illustrated, the pore comprises a central channel for convective flow and thin radial fins 32 which extend from the interior wall 34 of the pore and define a large surface area. At low fluid velocity, diffusion between the radially directed fins 32 and convective pore 14 would be required to access the solute interactive surfaces. Higher pressures would effect convective flow within throughpore 14 and axially within the spaces between radial fins 32, permitting convective transport of solutes in close proximity with the solute interactive surfaces disposed on the walls and fins.

Another form of perfusive matrix (not shown) comprises flow channels, such as relatively uniform pores in a membrane or a hollow fiber, having adhered to their interior walls fine particles comprising the solute interactive surface area. The subpores would be defined by the intersticies among the particles, the second pore set by the flow channels, and the first pore set by other flow paths disposed, for example, tangentially to the surface of the membrane, or among hollow fibers in a fiber bundle. Techniques for producing such structures are well known. The difference between existing structures of this general type and one designed for perfusive chromatography lie in the dimension of the first and second pore sets which are designed as set forth herein to promote convective flow in both types of channels.

From the foregoing it should be apparent that matrices of the invention may be embodies in many specific forms. They may be fabricated from inorganic materials as well as polymers.

OPTIMIZATION OF PERFUSIVE MATRIX MATERIALS

As discussed above, the throughpore Peclet number ($P_eII$) must exceed 1 to enter the perfusive domain. However, high PeIIs, at least 5 and most preferably greater than 10, are preferred. Perfusive behavior also is dependent on internal surface area. Therefore, it is important that subpores or other configurations providing the interactive surface be accessed readily. As an illustration of the parameters of design of such a matrix material, it may be instructive to examine the aggregative formation of particles of the type described above having a given poron diameter.

For a given particle size ($D_p$) the larger the flow channel ($d_p$) the fewer flow channels there can be per particle at a constant particle void fraction. Furthermore, the larger the flow channel, the larger the clusters have to be to form it, and thus the deeper the diffusive penetration required to access the surface area. The benefit of using fewer but larger holes is that perfusion takes effect at relatively lower bed velocities and corresponding pressure drops. Perfusion depends on bed velocity, and the upper limit of velocity is dictated by the pressure tolerance limit of the sorbent particles. At large particle diameters, as illustrated below, this constraint becomes less significant.

Figure 8:
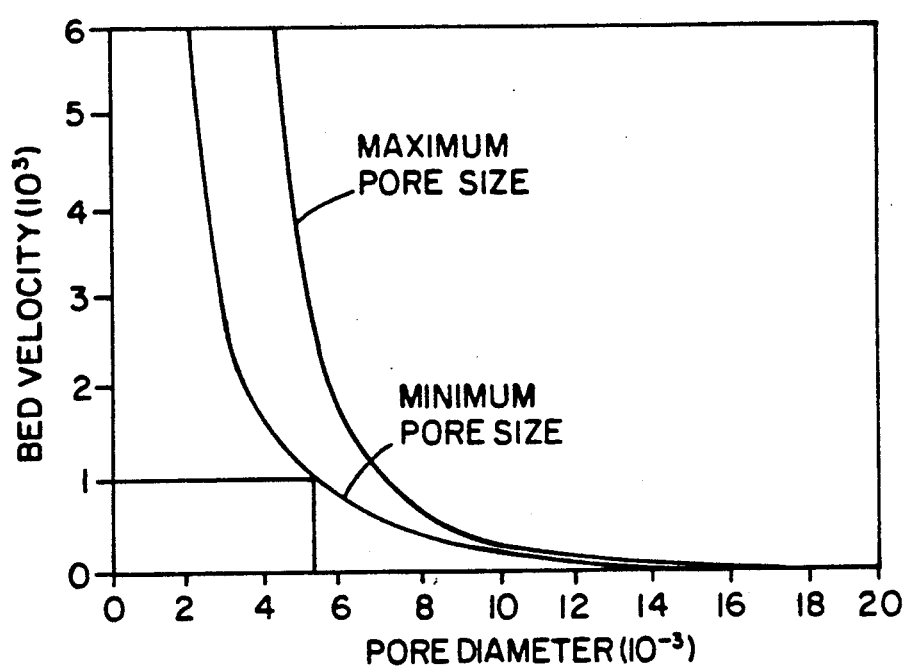
FIG. 8 is a graph of bed velocity in cm/hr vs. throughpore size in angstroms showing the maximum and minimum pore sizes able to achieve a Peclet number greater than 10 at a given diffusion coefficient and particle size.

FIG. 8 is a graph of bed velocity in cm/hr vs pore diameter in Å for a 10 μm nominal diameter particle bed. The graph shows the minimum and maximum throughpore size to achieve a throughpore Peclet number of 10 assuming a 10 μm particle, the diameter of the intraparticle flow channels is ⅓ of the particle size, and the characteristic pore diffusion time is less than convection time. Thus, for example, at 1,000 cm/hr, 10 μm particles require a mean pore diameter greater than about 5,000 Å in order to achieve a Peclet number of 10 or more. The curve labeled "maximum pore size" sets forth the maximum mean throughpore diameter, for various bed velocities, at which convective flow through the pore is so fast that solute diffusion in and out of the subpores is too slow to permit effective mass transfer to the interactive surfaces. Note that the minimum bed velocity needed to establish perfusion (with $P_eII > 10$) diminishes with increasing throughpore mean diameter. Note also that perfusion will not occur to any significant extent in conventional porous media ($<500$ Å pore size).

Figure 9:
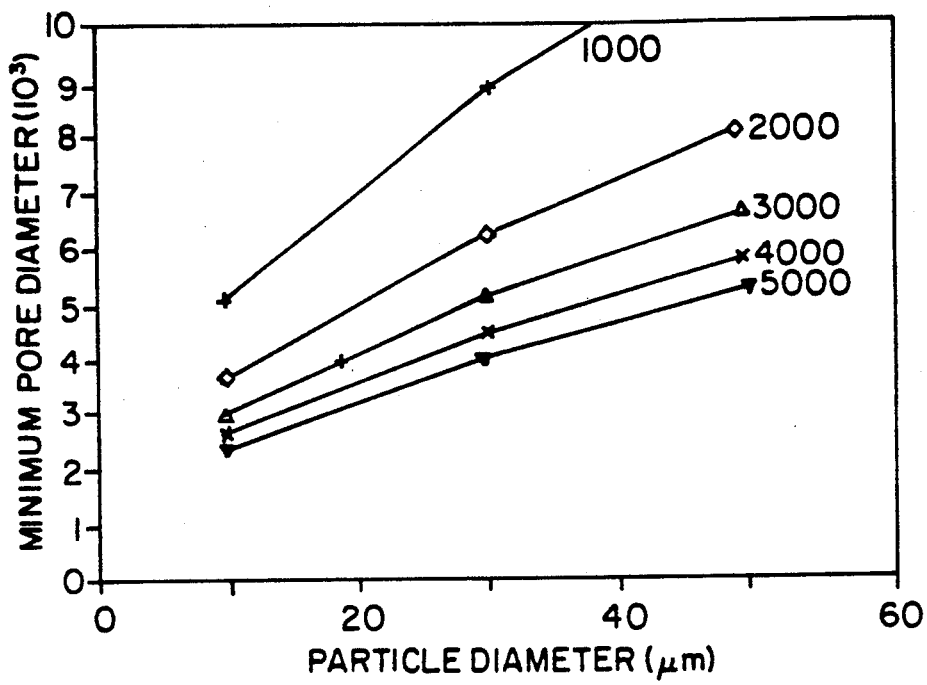
FIG. 9 is a graph of minimum pore mean diameter in angstroms vs. particles diameter in $\mu$m illustrating the perfusive domain at various Vbed given the assumptions disclosed herein.

FIG. 9 shows the minimum pore diameter (in thousands of angstroms) needed for various diameter particles (in μm) for various bed velocities, ranging from 1,000–5,000 cm/hr, required to achieve a Peclet number (PeII) greater than 10, making the same assumptions as discussed immediately above. Clearly, perfusion can be used with larger diameter particles. For example, a 50 μm particle with 1 μm flow channels, leading to 500 Å diffusive pores, would operate in a perfusive mode at bed velocities exceeding 800 cm/hr.

Analysis of the flow properties of perfusive chromatography matrices suggests that there are very significant advantages to be gained by using large particles having large throughpores leading to subpores. Where one seeks to maintain resolution, i.e. maintain plate height constant, by scaling up a bed having particle size $D_p1$ and throughpore size $d_p1$ then, at constant bed velocity, the size of the larger particles ($D_p2$) and their pores ($d_p2$) is given by the expression $$\left(\frac{D_p^2}{D_p^1}\right) = \left(\frac{d_p^2}{d_p^1}\right)^{2/3} \quad \text{(Eq. 9)}$$

To scale up at constant plate height and constant total pressure drop, the relationship is:

$$\left(\frac{D_p^2}{D_p^1}\right) = \left(\frac{d_p^2}{d_p^1}\right)^{2} \quad \text{(Eq. 10)}$$

and in general:

$$\left(\frac{D_p^2}{D_p^1}\right) = \left(\frac{\Delta_p^2}{\Delta_p^1}\right)\left(\frac{d_p^2}{d_p^1}\right)^{2} \quad \text{(Eq. 11)}$$

As is evident from a study of the foregoing relationships, a linear particle size/pore size scale-up allows the same separation to be performed faster and at lower pressure drops. This behavior is counterintuitive based on current chromatography theory and practice.

To illustrate this scale-up concept, note, from Equation 10, that by increasing the pore size by a factor 5, the plate height of a 50 μm perfusive particle becomes equal to that of 10 μm perfusive particle at 25 times higher velocity and the same pressure drop. In order to operate at a lower pressure drop, the same bed velocity, but with larger particles, the pore size would have to increase even more to accommodate a constant plate height upon scale-up (see Equation 9). An increase in pore size by about 11 fold is needed to achieve an equivalent resolution separation at 25 times lower pressure drop. From Equation 11 it should be apparent that, for example, with 50 μm particles, an increase in bed velocity of 5 fold, a pressure drop decrease of 5 fold, and a pore diameter increase 5 fold will achieve the same resolution faster and at lower pressure drop than for a 10 μm particle.

The table set forth below illustrates these relationships for six case studies. Column one in each case requires a 5 fold increase in particle size. In case A, the pore size in the larger particle remain unchanged and the same superficial bed velocity is used (Column 4). In this case, relative to the bed of smaller particles, the larger particle bed operates at a pressure drop of 1/25th (Column 3) and has a throughpore velocity of 1/25th (Column 5). However, the Peclet number in the throughpores of the larger particle is only 1/5 that of the smaller, and plate height increases by a factor of 125, greatly decreasing resolution.

In case B, pore size remains constant (Column 2) and superficial bed velocity is increased by a factor of 5 (Column 4). In this case, the pressure drop is only 1/5, as is the pore velocity. Peclet number remains constant, but plate height increases by a factor of 25.

In case C, pore size and operating pressure remain constant, resulting in a bed velocity 25 times that of the smaller particle bed. Velocity through the pores also remains constant, the Peclet number increases by a factor of 5 and plate height increases by a similar factor.

In case D, the throughpores of the particle are scaled-up by the same factor as the particle diameter, and pressure drop is maintained, resulting in a 25 fold increase in superficial bed velocity. The throughpore fluid velocity therefore increases by a factor of 5, the Peclet number increases by a factor of 25, and plate height remains constant.

In case E, the diameter of the throughpores is increased by a factor of 125 (5 relative to the particle diameter). Thus, at the same bed velocities, the pressure drop is 25 times higher than that in the smaller particle case. Fluid velocity in the throughpores if five times higher, the Peclet number increases by a factor of 25, and plate height stays the same.

Lastly, in case F, where the throughpore is scaled the same way as the particle size, operating at 5 times the bed velocity one experience only 1/5 the operating pressure. Yet the fluid velocity in the throughpores is 5 times that of the base case, the Peclet number is increased by a factor of 25, and plate height, and thus resolution, stay the same.

TABLE

| 1 $\frac{D_{p2}}{D_{p1}}$ | 2 $\frac{d_{p2}}{d_{p1}}$ | 3 $\frac{\Delta P_2}{\Delta P_1}$ | 4 $\frac{V_{B2}}{V_{B1}}$ | 5 $\frac{V_{p2}}{V_{p1}}$ | 6 $\frac{Pe_{II2}}{Pe_{II1}}$ | 7 $\frac{H_2}{H_1}$ |
|---|---|---|---|---|---|---|
| A | 5 | 1 | 1/25 | 1 | 1/25 | 1/5 | 125 |
| B | 5 | 1 | 1/5 | 5 | 1/5 | 1 | 25 |
| C | 5 | 1 | 1 | 25 | 1 | 5 | 5 |
| D | 5 | 5 | 1 | 25 | 5 | 25 | 1 |
| E | 5 | 125 | 25 | 1 | 5 | 25 | 1 |
| F | 5 | 5 | 1/5 | 5 | 5 | 25 | 1 |

In the foregoing analysis, Column 6, showing the ratio of Peclet numbers, is an indication of the advantage in productivity achieved over diffusive particles. The plate height ratio is an indication of the advantage (disadvantage) in resolution achieved over smaller perfusive particles. Thus, in cases D, E, and F, very significant increases in throughput and/or reduced pressure drop are achieved while maintaining the resolving power of smaller particles.

Accordingly, it is apparent that many trade offs can be made in order to best utilize the perfusive mode of solute transport in chromatography systems embodying the invention. It should also be apparent that large particles, e.g., greater than about 40 μm in diameter, having larger throughpores leading to subpores on the order of 300 to 700 angstroms in mean diameter represent a class of matrix materials of great promise.

EXEMPLIFICATION

The advantages of perfusion chromatography have been well demonstrated using the commercially available particulate media discussed above (PL 1,000 and PL 4,000) both untreated and derivatized with polyethyleneimine, and also with prototype materials manufactured by Polymer Laboratories, Ltd. similar to the PL 4,000 material but having a larger particle diameter. Tests were run using synthetic mixtures of proteins of the type generally encountered in protein purification and separation tasks.

Figure 10:
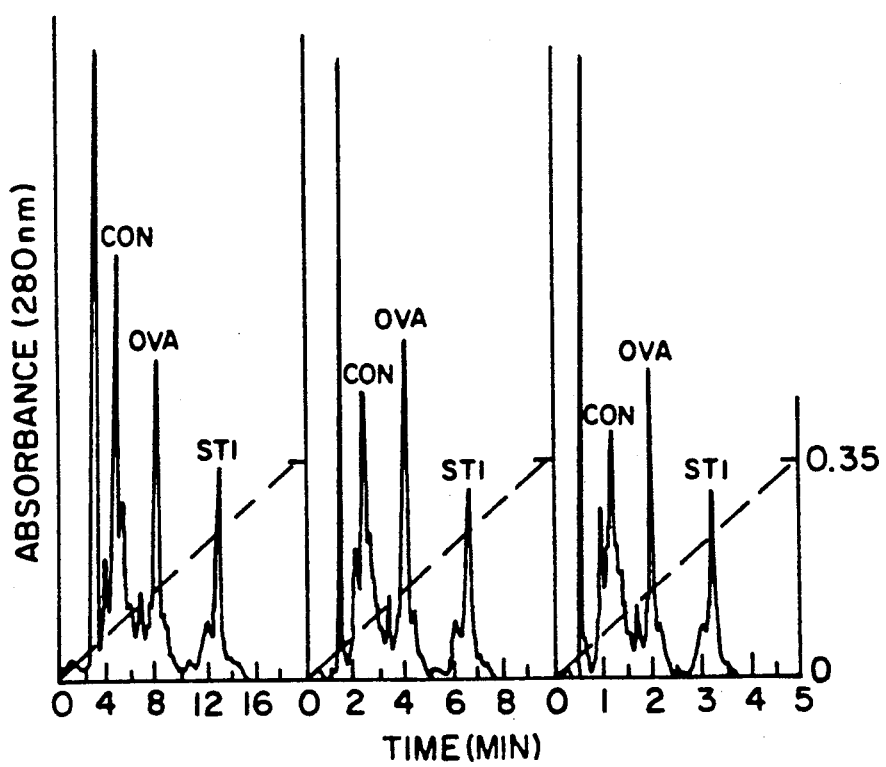

Evidence that, unlike conventional chromatography, bandspreading is not exacerbated by high flow rates in the perfusive chromatography realm is set forth in FIG. 10. These chromatograms, prepared by detecting by optical absorption the protein output of a 50 mm by 4.6 mm column packed with PL 4,000 material, show quite clearly that the resolution of, for example, the proteins OVA (ovalbumin) and STI (soybean trypsin inhibitor) are similar at 1 ml per minute (350 cm/hr), 2 ml per minute (700 cm/hr), and 4 ml per minute (1400 cm/hr), left to right in FIG. 10). These chromatograms achieved, respectively, resolutions of 6.0, 6.5, and 6.2.

Figure 11:
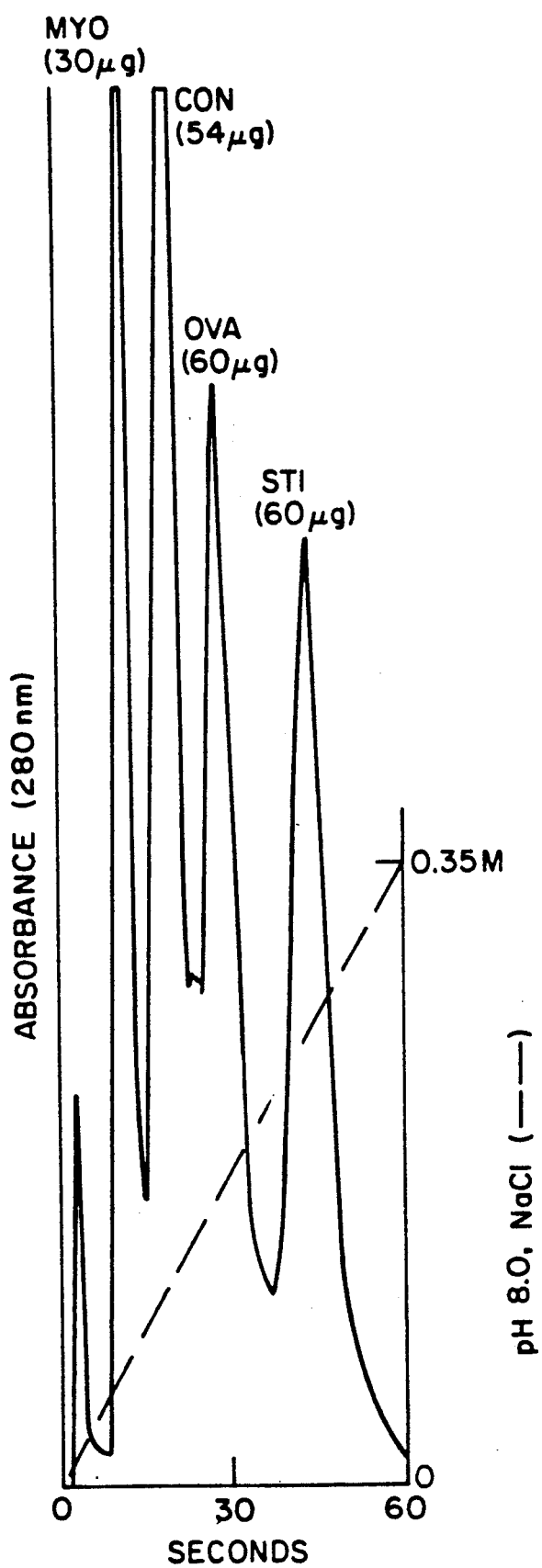

FIG. 11 shows data illustrative of the ability of perfusive chromatography to produce high resolution very rapid separations of protein at high bed velocities and shallow column geometries. FIG. 11 was produced with a 5 mm long by 6 mm wide column using PL 4,000 material with a flow rate of 3 ml per minute. Note the resolution of the four test proteins in less than 1 minute.

Figure 12:
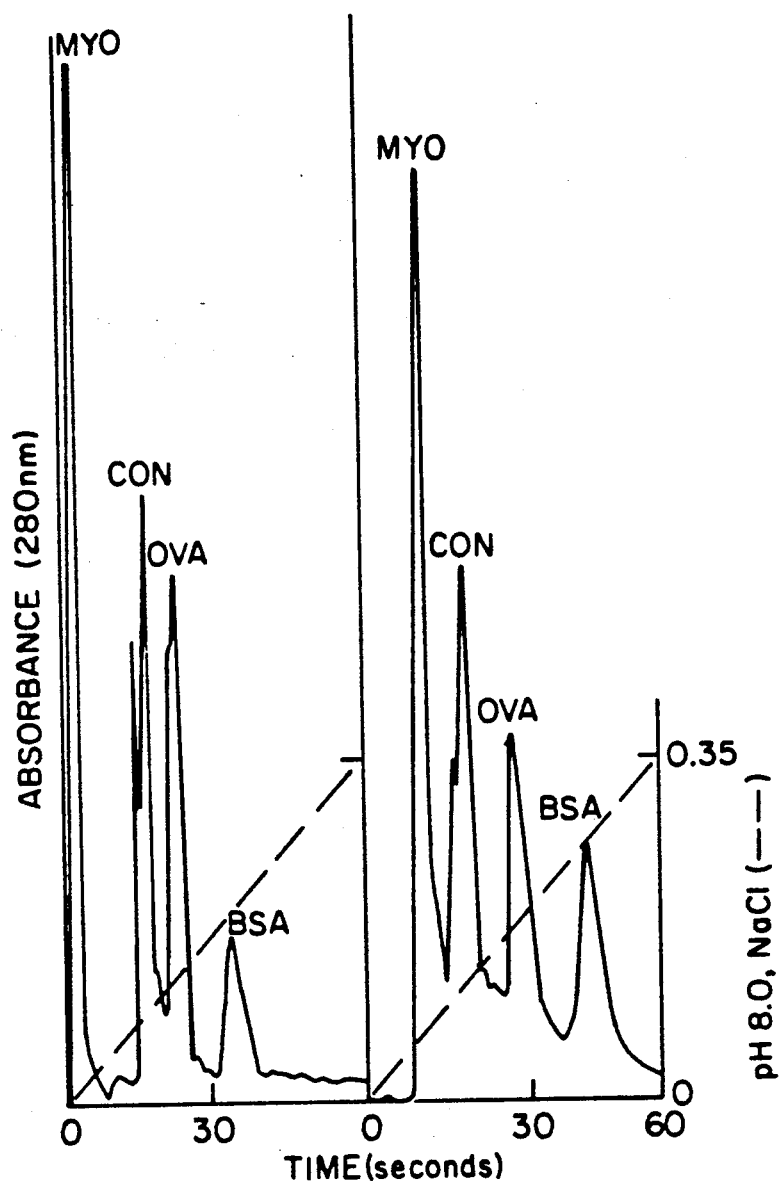
Figure 13A:
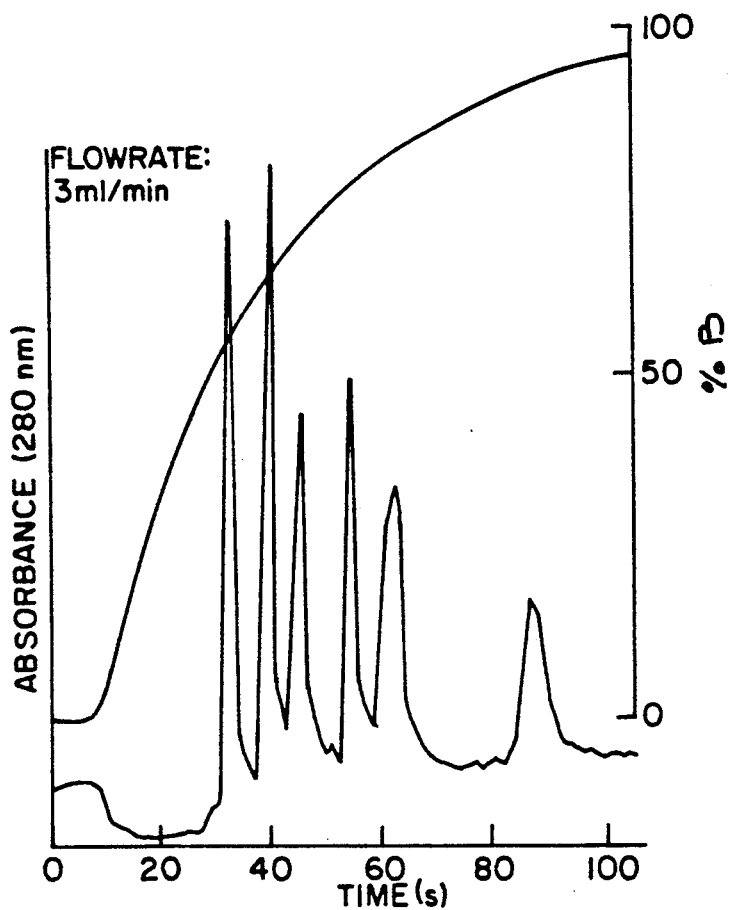
Figure 13B:
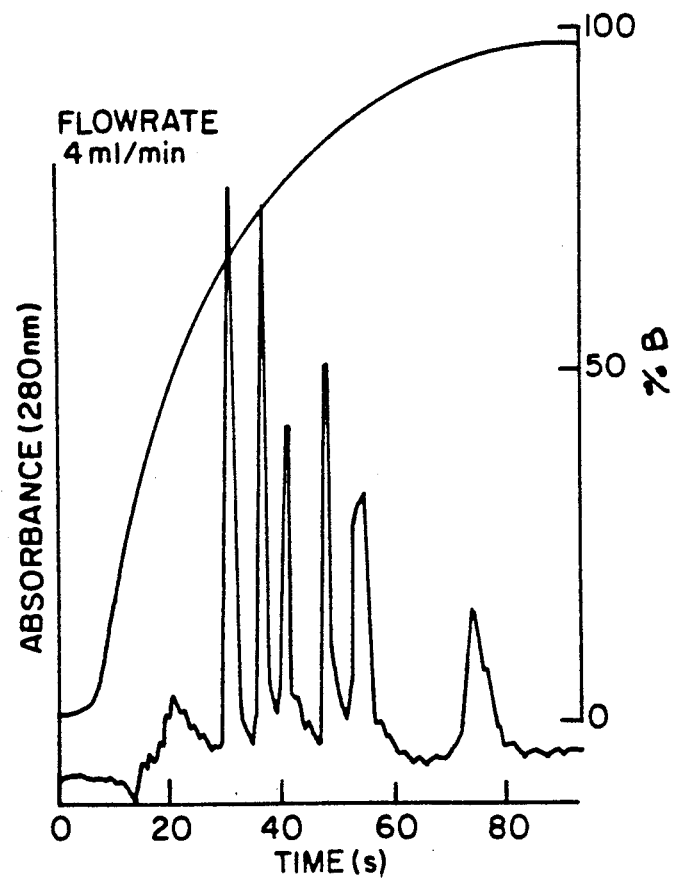
Figure 13C:
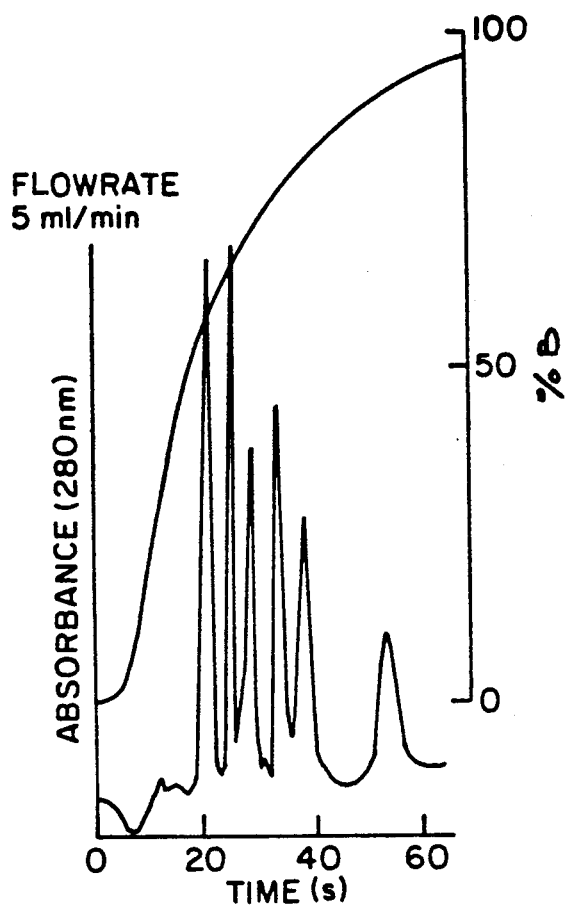
Figure 13D:
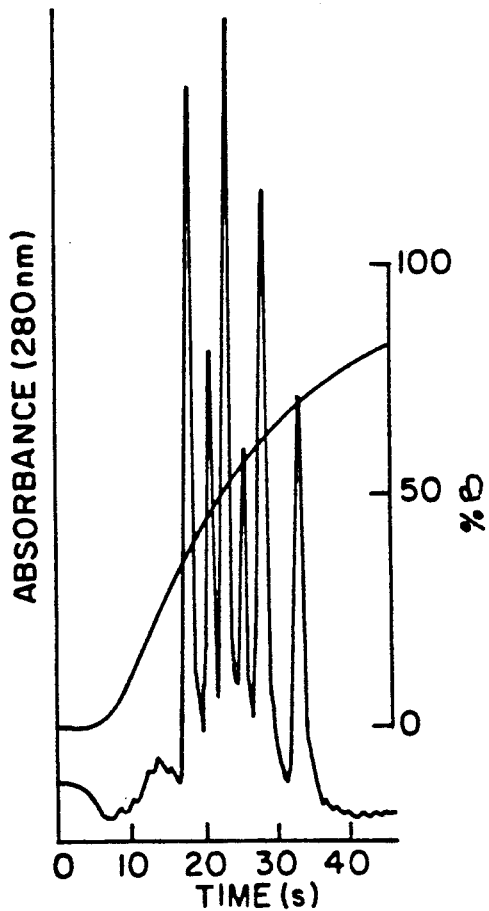

FIG. 12 compares the performance of nonporous vs perfusive media for the separation of the test protein mixture. PL 4,000 material (right) is seen to perform in comparable fashion to the nonporous particles (left) in spite of the much larger size of the PL material (10 $\mu$m vs. 3 $\mu$m). This is in contrast to diffusive media where resolution typically is related inversly to the square of the particle diameter.

FIG. 13A through 13D show high resolution separations of 6 proteins in less than 90, 80, 60, and 40 seconds, respectively, at bed velocities of 900, 1200, and 1500 cm/hr and 1200 cm/hr respectively, using the PL 4,000 underivatized particles (reverse phase). These chromatograms were produced on a 6 mm by 5 mm column with a gradient of trifluoroacetic acid and acetonitrile. Chromatogram 13D was achieved by using a steeper gradient.

Figure 14:
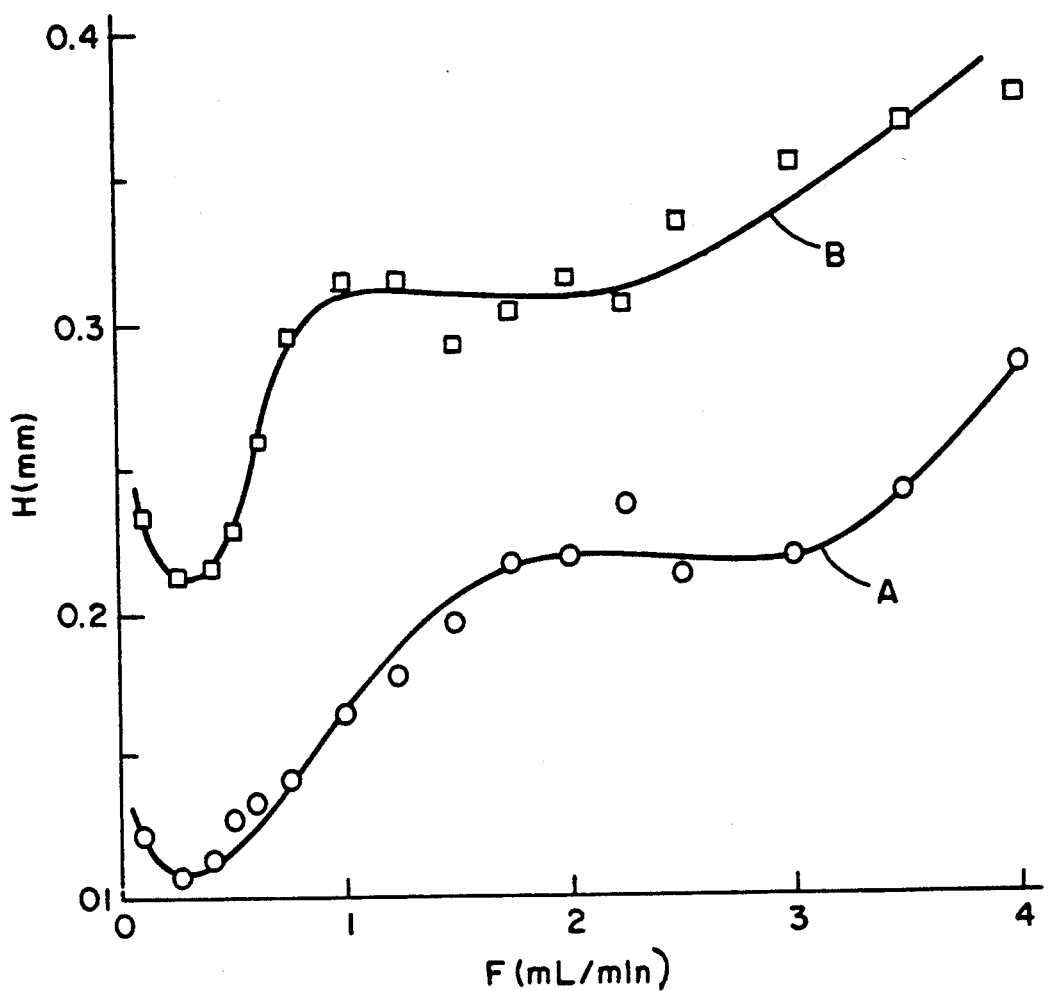

FIG. 14 provides further evidence of the contribution of convective transport to perfusive chromatography procedures. It discloses plate height curves (H vs. flow rate) for lysozyme (A) and acid phosphatase (B) produced using a 250 mm by 4.5 mm column packed with the PL 4,000 material eluted with 250 mM NaCl. As illustrated, at low mobile phase velocity, the plate height curves are indistinguishable from conventional matrix material. That is, below about 1 ml/min, the plate height is seen to increase with increase flow rate. However, at high mobile phase velocities, in the range of 1 to 2 ml/min for acid phosphatase, and 2 to 3 ml/min for lysozyme, the plate height curve is actually flat. At very high velocities, i.e., above about 700–800 cm/hr for acid phosphatase and about 1100 cm/hr for lysozyme, the plate height rises again, but at a much slower rate than expected for the severe diffusion limitations that would prevail under these conditions in conventional media.

Figure 15A:
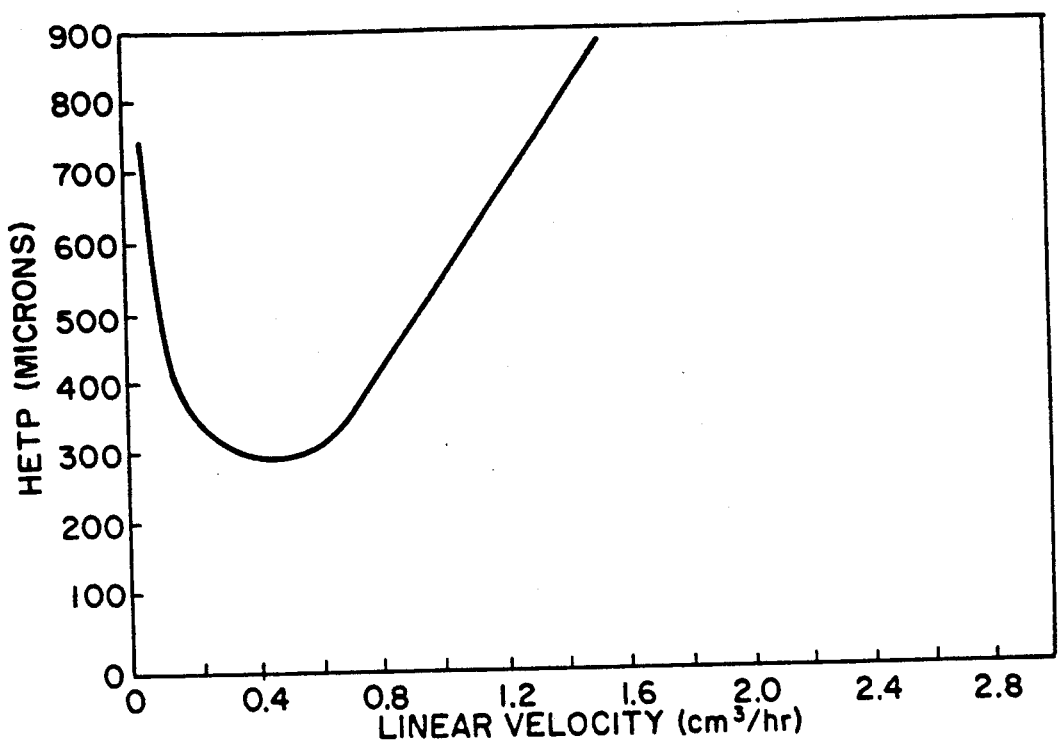
Figure 15B:
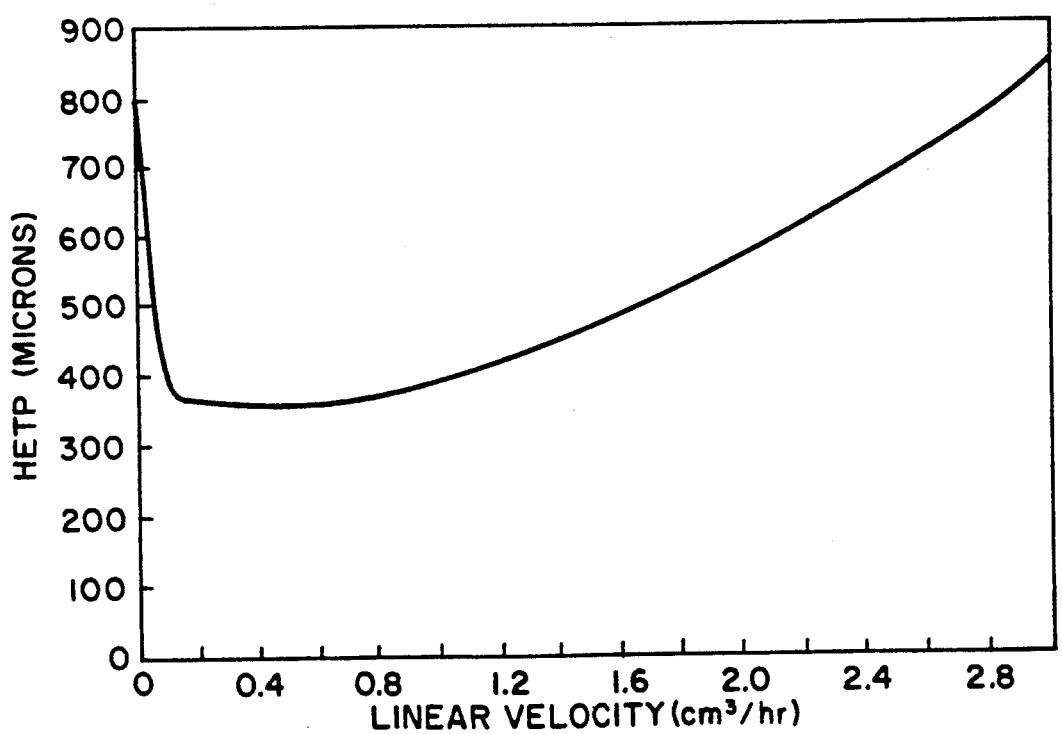

FIG. 15A and 15B compare the plate height curves for various linear flow velocities for, respectively, a diffusively bound polymer bead (Monobeads, Phamarcia) and the PL 4,000 material. Because of pressure limitations, the Monobeads could not be used at a velocity greater than about 1200 cm/hr. At linear velocities as high as 2500 cm/hr, bandspreading with the PL 4,000 particles is less than twice its value at the minimum. In contrast, by extrapolating this stagnant mass transfer limited regime of FIG. 15A, this value would be nearly four times higher than minimum for the conventional Monobead medium.

Figure 16A:
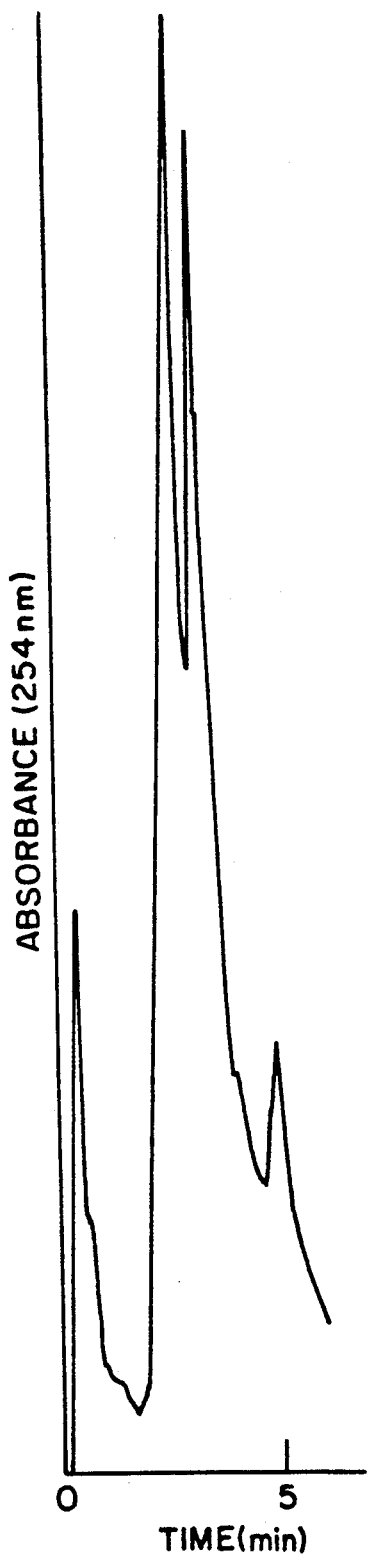
Figure 16B:
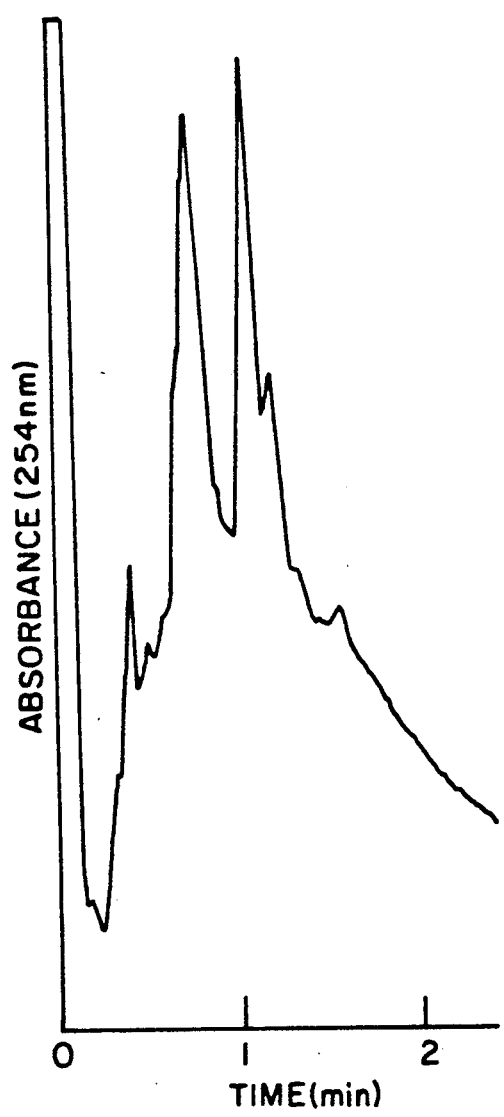
Figure 16C:
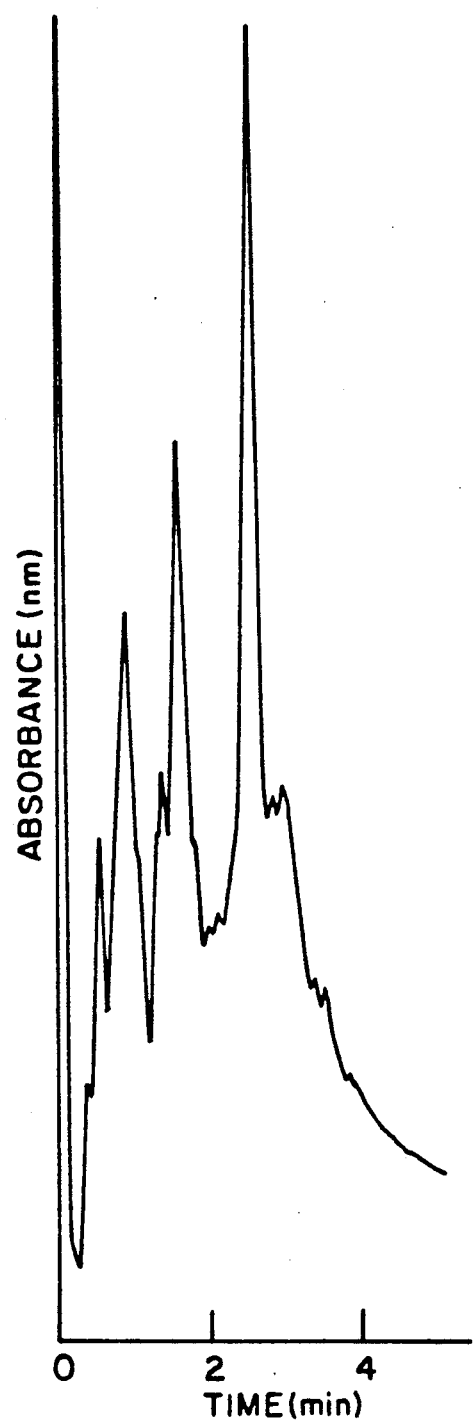
Figure 18A:
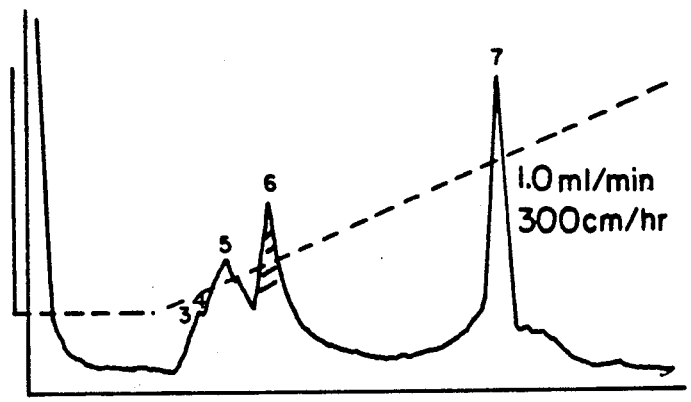
Figure 18B:
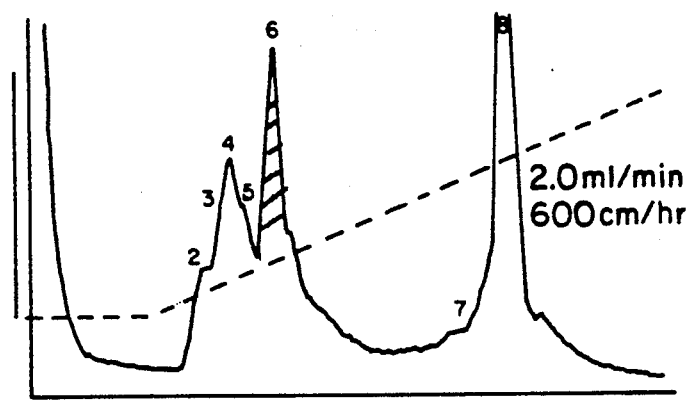
Figure 18C:
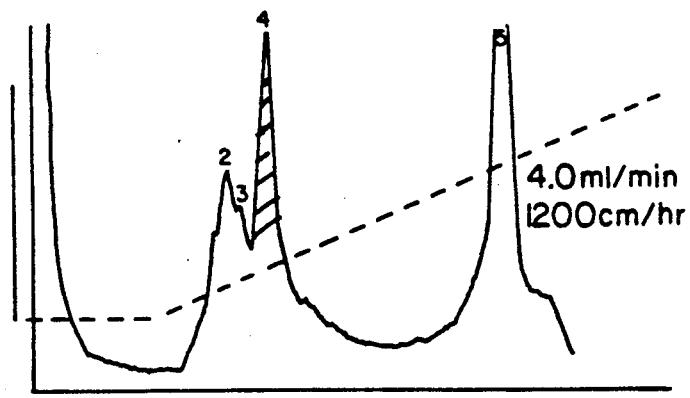
Figure 18D:
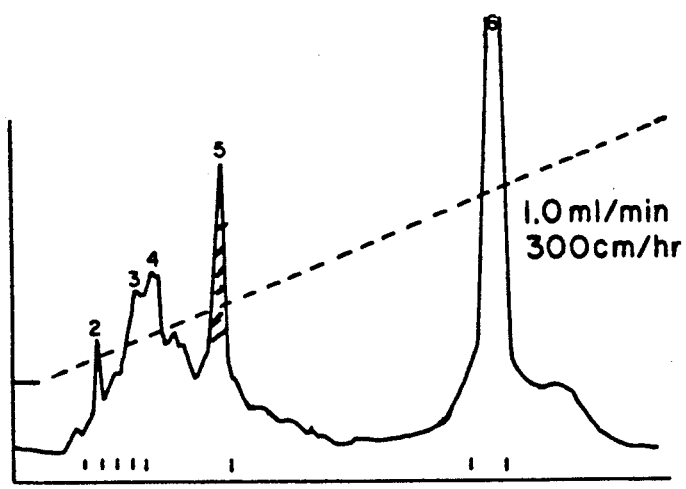
Figure 18E:
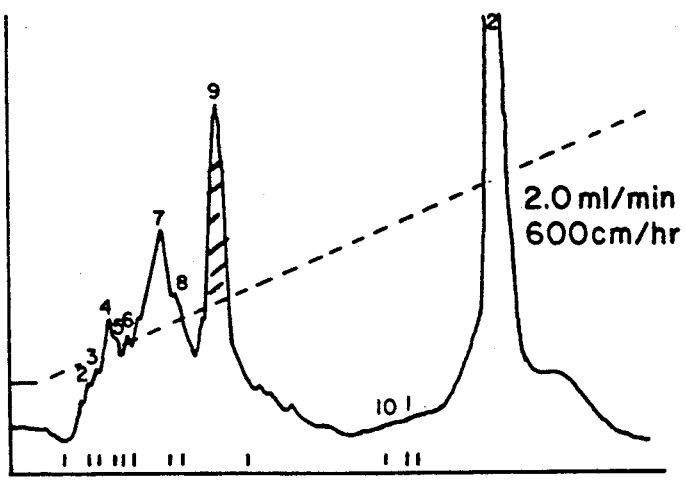
Figure 18F:
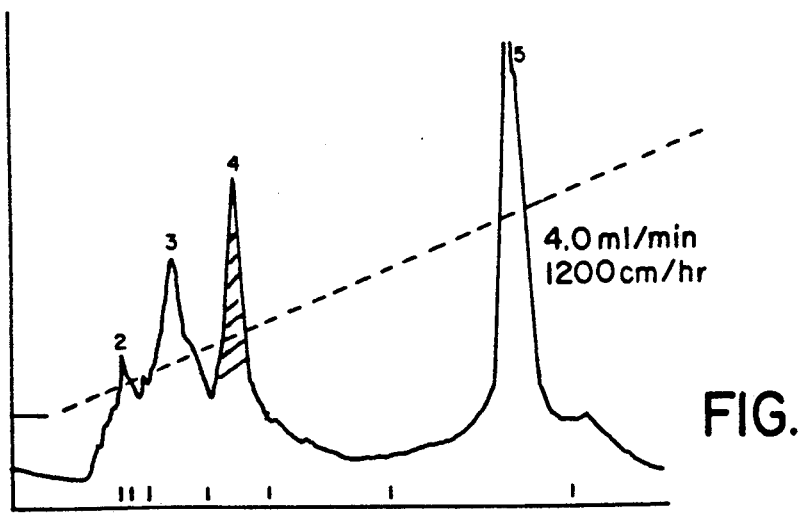

One ramification of the enhanced transport kinetics characteristic of perfusive chromatography is a short cycle time. However, the perfusive enhancement also can be used to increase resolution with the same cycle time. This is illustrated in FIGS. 16A, 16B, and 16C, chromatograms showing the separation of a complex protein mixture using the PL 4,000 material. At 350 cm/hr (16A), the procedure is diffusion limited (Peclet number in the throughpores less than 1). Separation is fair with a steep gredient of 40 mM $CaCl_2$/minute. As shown in FIG. 16B, cycle time can be shortened considerably by increasing the bed flow rate to 4300 cm/hr. As illustrated in FIG. 16C, by using a bed linear velocity of 4300 cm/hr with a shallower gradient of 12 mM $CaCl_2$/minute, one can obtained a much higher resolution in a shorter time frame.

FIGS. 17A and 17B show that peak resolution is not affected by an increase in bed velocity of greater than tenfold for separation of IgG class 1 and 2. The chromatogram of FIG. 17A was run on a 30 by 2.1 mm column of the PL 4,000 material. The immunoglobulins from mouse ascites were separated with a 40 mM $CaCl_2$/min gradient at a flow rate of, respectively, 0.2 ml/min, and 2.5 ml/min, representing fluid velocities of 300 cm/hr and 4300 cm/hr, respectively.

FIGS. 18A through 18F are chromatograms produced by purifying Beta-Galactosidase from *E. coli* lysate on the PL 4,000 (A, B, C) and PL 1,000 (D, E, F) materials. As illustrated, a full cycle can be performed in less than 15 minutes in the perfusive mode (1200 cm/hr, 18C, 18F) giving essentially the same performances in resolution as obtained in a typical 60 minute cycle 300 cm/hr (18A, 18D). The beta-gal peak is shaded.

Figures 19A, 19B:
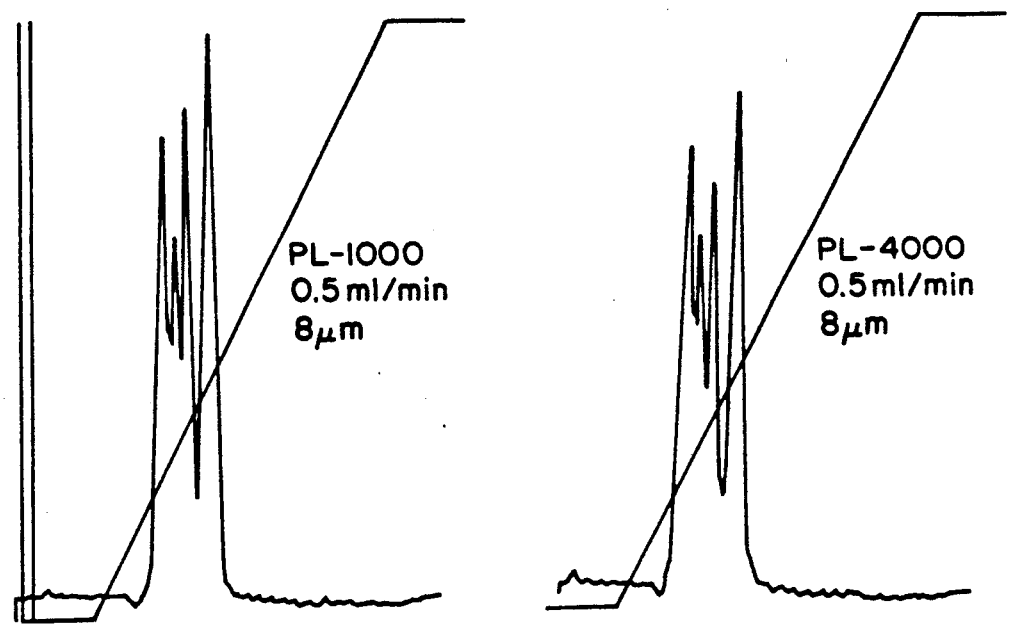
Figures 19C, 19D:
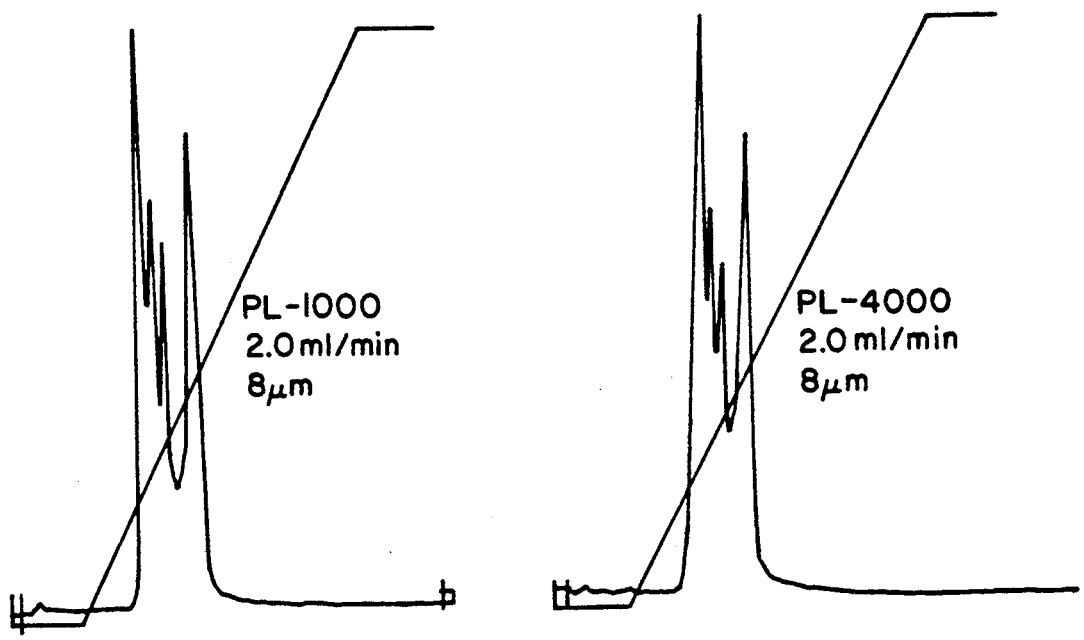
Figure 19E:
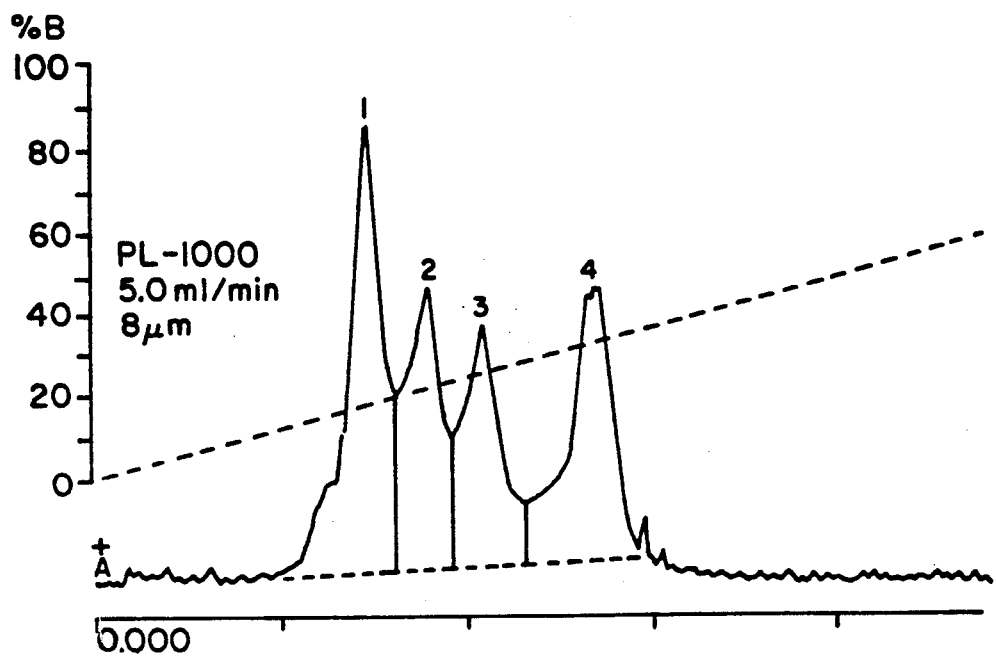
Figure 19F:
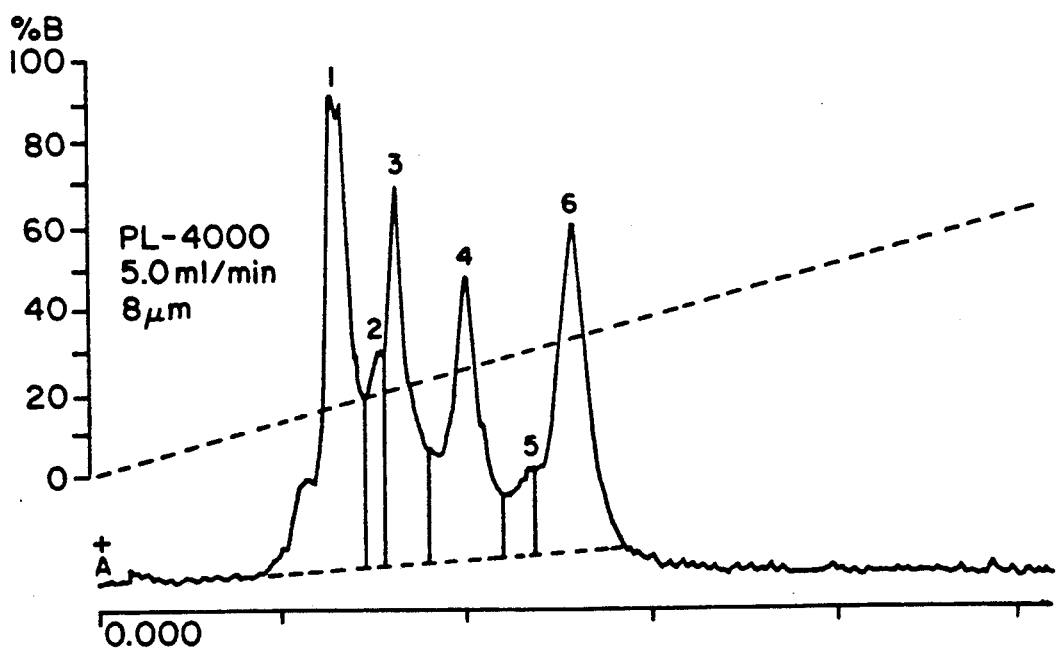
Figure 20A:
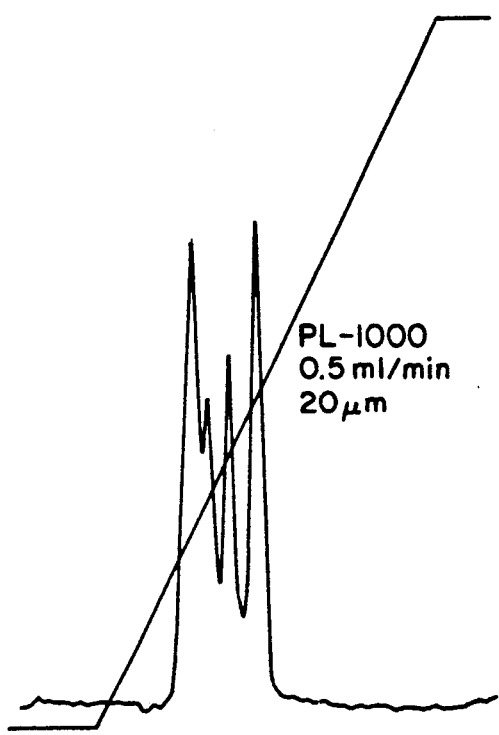
Figure 20B:
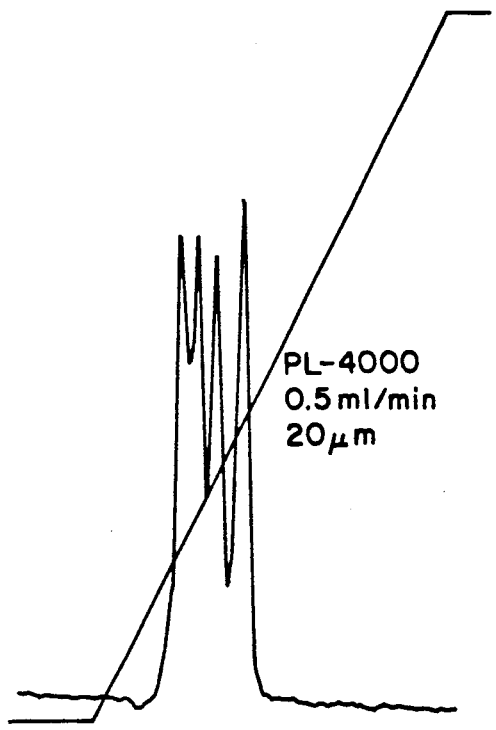
Figure 20C:
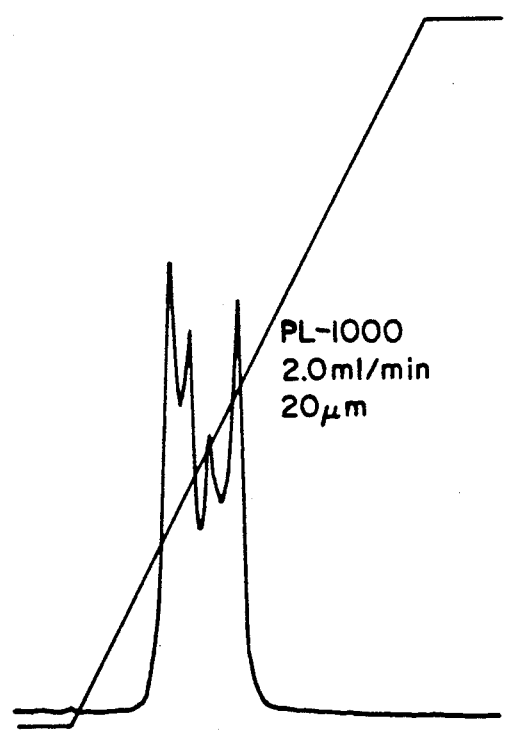
Figure 20D:
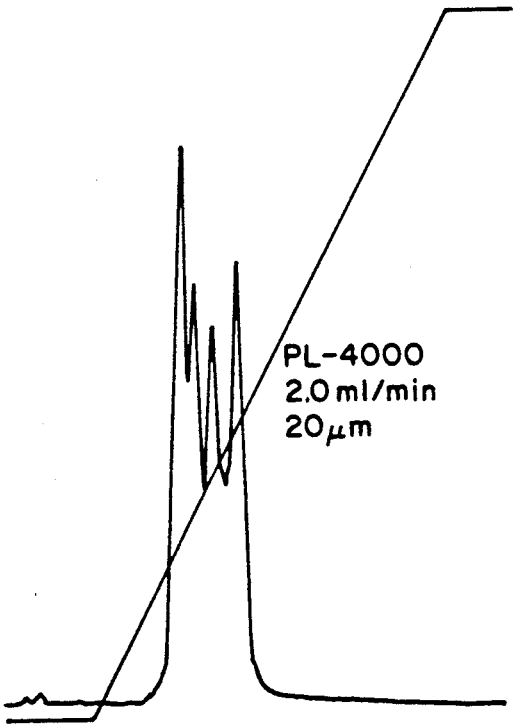
Figure 20E:
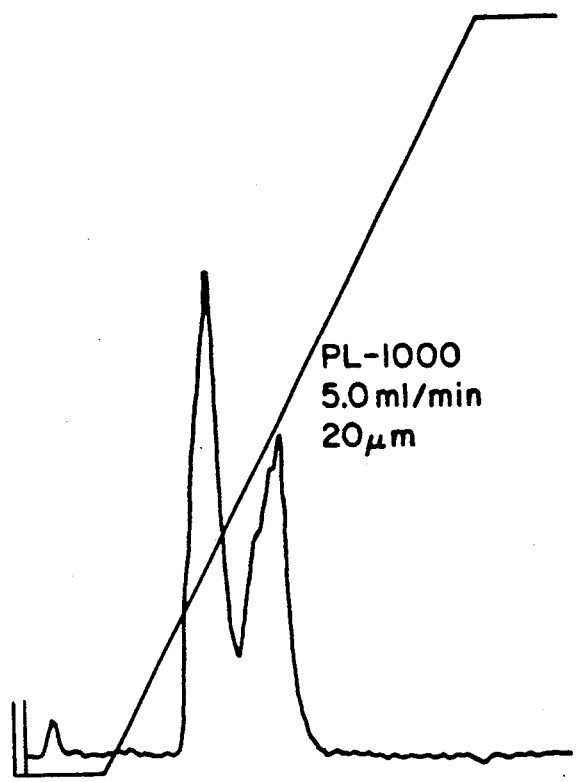
Figure 20F:
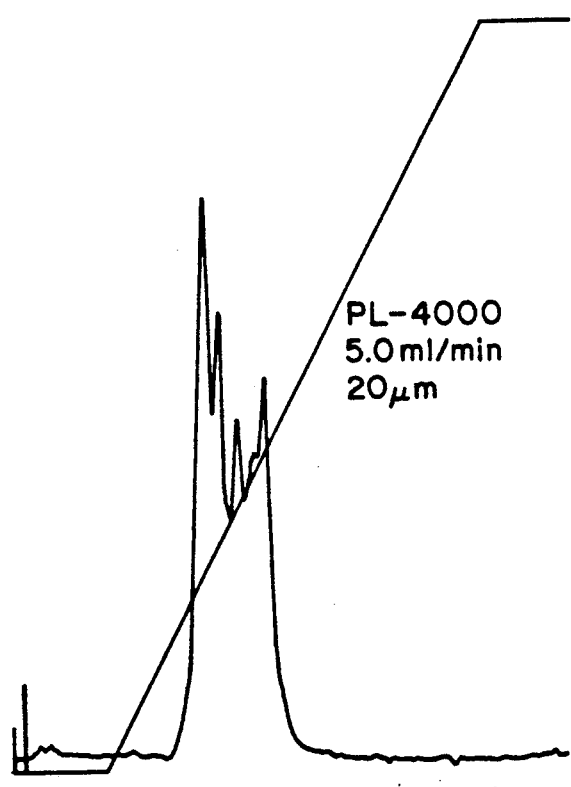

FIG. 19A, B, C and D show four chromatograms produced by separating a test protein mixture containing beta lactoglobulin and ovalbumin with the strong ion exchange versions of the PL 1,000 and PL 4,000 materials. This test mixture was separated with columns packed with the particle noted and operated at 0.5 and 2.5 ml/min. With 8 micron particles, the separation is the same at 0.5 ml/min (19A, 19B), and at 2.5 ml/min. (19C, 19D). As shown in FIGS. 19E and 19F, at 5.0 ml/minute, the PL 4,000 material performed better than the PL 1,000, since it perfuses to a higher extent. Nevertheless, both separate the mixture adequately.

Conventional liquid chromatography teaching, well corroborated by experiment, is that "increasing particle size leads to a lower resolution at a given flow rate, and with increasing flow rates the loss in resolution is increased at a faster rate". However, as noted above, with perfusive matrices, the degree of perfusion is dependent on the relative size of the first and second pore sets, which, for particulate media, translate to relative particle diameter and throughpore size. Separation performance in a perfusive regime with large particles therefore is expected to depend less on flow rate.

The validity of this hypothesis is demonstrated by comparison of FIGS. 19 with FIGS. 20. FIGS. 20A and 20B were produced with the protein sample at 0.5 ml/min using PL 1,000 and PL 4,000 particles, respectively, both having a 20 $\mu$m mean particle size. FIGS. 20C and 20D were run with PL 1,000 and 4,000 materials, both 20 $\mu$m particle size, at 2.0 ml/min. FIGS. 20E and 20F were run at 5.0 ml/min using the respective materials. The data show that at 0.5 ml/min, the PL 4,000 material performed slightly better than the PL 1,000 material, and, as expected, when operating at flow rates too low to induce perfusion, both perform worse than their 8 μm particle size counterparts. At 2.0 ml/minute, the gap in performance between these two materials widens, with the PL 1,000 material losing resolving power considerably while the PL 4,000 material can still separate the peaks. At 5.0 ml/minute (1500 cm/hr) the 20 μm 4,000 angstrom material can still resolve these peaks while the PL 1,000 material loses performance almost completely. The difference between the performance of the two materials is less at 8 μm than at 20 μm because, while both perfuse in the smaller particle case (to different extents), with the larger particles the PL 1,000 materials are expected to perfuse very little in comparison with the 4,000 material.

Figure 21:
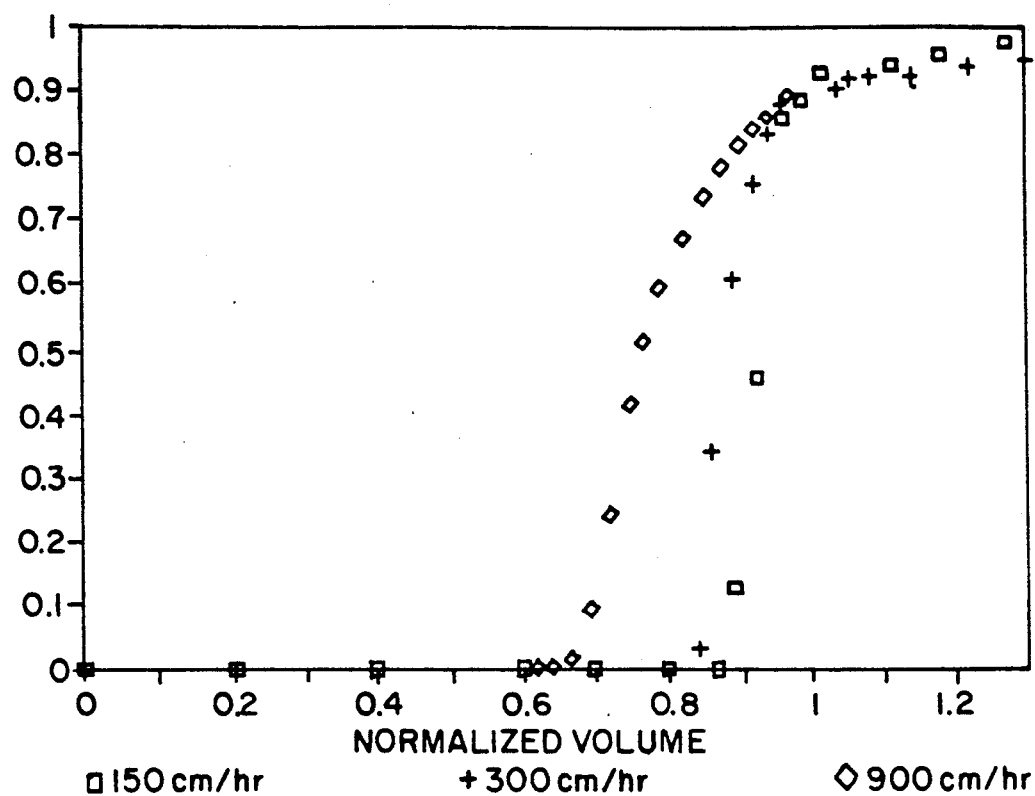
Figure 22:
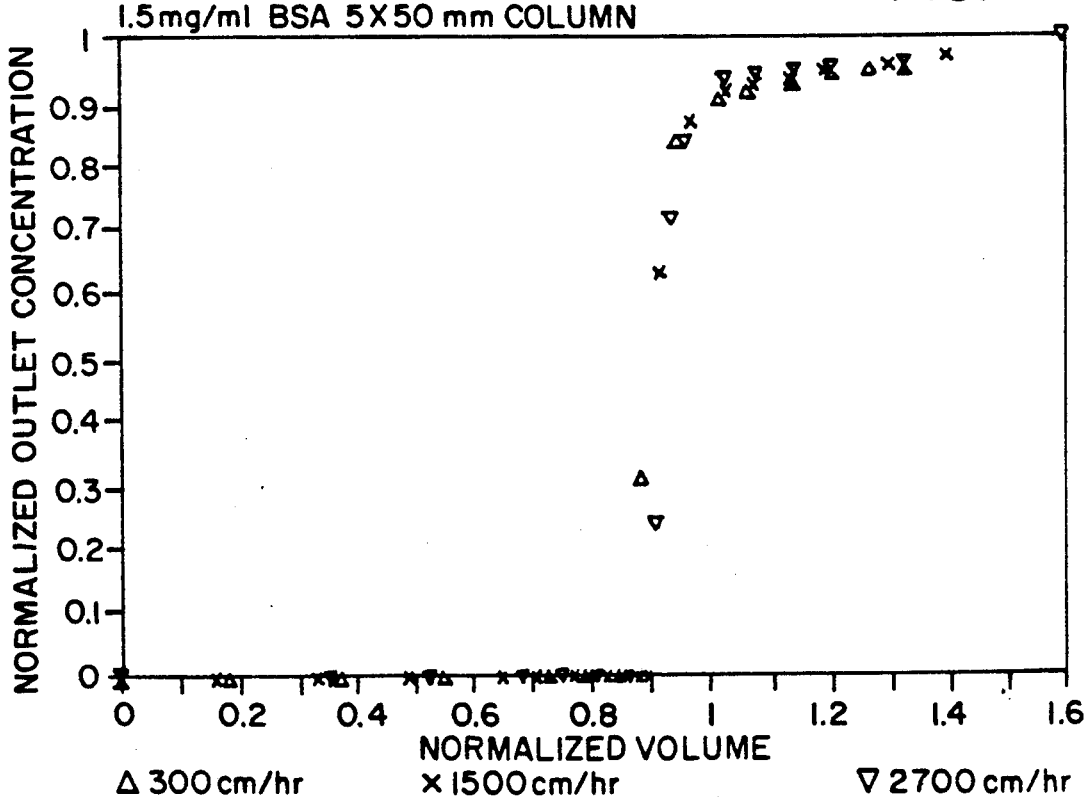

Lastly, FIG. 21 and 22 provide experimental verification of the calculations discussed above for the difference in breakthrough behaviors between perfusive particles and conventional porous, diffusive bound particles. FIG. 21, made in a 5 by 50 mm column using Monobeads (Pharmacia) to separate BSA, shows that, at 150 cm/hr, the breakthrough curve is shaped as expected for a diffusive column operated under equilibrium conditions. As the fluid velocity is increased to 300 cm/hr, deviation from the equilibrium curve begins and at 900 cm/hr premature breakthrough is clearly evident. In contrast, as shown in FIG. 22, using PL 4,000 in the same column to separate the same protein, the breakthrough curves are essentially equivalent at 300, 1500, and 2700 cm/hr.

The invention may be embodied in other specific forms without departing from the spirit and essential characteristics thereof. Accordingly, other embodiments are within the following claims.

What is claimed is:

1. A chromatography method comprising the steps of:
   (A) forming a chromatography matrix by packing a multiplicity of particles defining throughpores and solute interactive surface regions therewithin; and
   (B) passing a fluid mixture of solutes comprising biological molecules through said matrix at a velocity sufficient to induce a convective fluid flow rate through said throughpores greater than the rate of solute diffusion through said throughpores and to produce a Peclet number in a said throughpore greater than 1.0.

2. A chromatography method comprising the steps of:
   (A) providing a chromatography matrix defining:
      interconnected first and second throughpore sets, the members of said first throughpore set having a greater means diameter than the members of said second throughpore set, and
      surface regions in fluid communication with the members of said second throughpore set which reversibly interact with a solute, and
   (B) passing a fluid mixture of solutes comprising biological molecules through said matrix at a rate sufficient
      to induce convective fluid flow through both said throughpore sets and
      to induce a convective flow rate within said second throughpore set greater than the rate of diffusion of said solute within said second throughpore set, thereby to produce a Peclet number in a said second throughpore greater than 1.0.

3. The method of claim 1 or 2 wherein the chromatography matrix defines a multiplicity of subpores comprising said surface regions.

4. The method of claim 3 wherein said fluid mixture is passed through said matrix at a rate such that the time for said solute to diffuse to and from a said surface region from within a member of said second throughpore set is no greater than ten times the time for solute to flow convectively past said region.

5. The method of claim 3 wherein said subpores have a mean diameter less than about 700 Å.

6. A chromatography method comprising the steps of
   A. providing a chromatography matrix defining:
      interconnected first and second throughpore sets, each of which comprises a multiplicity of pores for channeling through said matrix a mixture of solutes disposed in a fluid, and
      surface regions in fluid communication with the members of the second throughpore set which sorb a solute in said mixture
   B. passing a fluid mixture of solutes comprising biological molecules through said matrix at a fluid flow rate sufficient to produce:
      convective fluid flow through both throughpore sets,
      a convective fluid flow velocity through said first throughpore set greater than the fluid flow velocity through the second throughpore set, and
      a convective fluid flow velocity through said second throughpores et greater than the diffusion rate of said solute within a member of said second throughpore set whereby the Peclet number therein is greater than 1.0, to load solutes from said fluid mixture onto said surface regions, and
   C. passing an eluant through said matrix to elute a fraction rich in a selected one of said solutes.

7. The method of claim 6 wherein the relative dimensions of the members of said second throughpore set and said surface regions permit flow through the members of said second throughpore set at a rate such that the time for a solute to diffuse to and from said surface regions from said second throughpore set is comparable to or shorter than the time for said solute to flow convectively past said region.

8. The method of claim 6 wherein step B or C is conducted by passing said fluid mixture or eluant through said matrix at a bed velocity greater than 1500 cm/hr.

9. The method of claim 6 wherein step B or C is conducted by passing said fluid mixture or eluant through said matrix at a bed velocity greater than 1000 cm/hr.

10. The method of claim 6 wherein the step B and C are conducted at fluid flow velocities through the matrix to produce a specific productivity of at least 1 mg total solute sorbed per ml of matrix per minute.

11. The method of claim 6 wherein the step B and C are conducted at fluid flow velocities through the matrix to produce a specific productivity of at least 2 mg total solute sorbed per ml of matrix per minute.

12. The method of claim 6 wherein the matrix provided in step A comprises packed particles having a mean diameter greater than 8 μm, said second throughpore set comprises throughpores within the particles having a mean diameter greater than 2000 Å, and the ratio of the mean diameter of the particles to the mean diameter of the throughpores is less than 70.

13. The method of claim 6 wherein the ratio of the mean diameter of the particles to the mean diameter of the throughpores is less than 50.

14. The method of claim 2 or 6 wherein one of said throughpore sets comprise pores having a narrow distribution of pore diameters such that 90% of the pores fall within 10% of the mean pore diameter.

15. The method of claim 2 or 6 wherein at least one of said throughpore sets comprises a plurality of subsets having differing means diameters together producing a wide distribution of pore diameters.

16. The method of claim 1, 2, or 6 comprising the additional step of collecting a selected one of said solutes after step B.

17. The method of claim 6 wherein said surface regions comprise subpores having a mean diameter less than about 700 Å.

18. The method of claim 6 wherein the fluid is passed through the matrix in step B or C at a velocity such that the Peclet number in the throughpores of the second throughpores set is greater than 5.

19. The method of claim 6 wherein the Peclet number in the throughpores of the second throughpore set is greater than 10.

20. A chromatography method comprising the steps of:
(A) providing a chromatography matrix defining:
interconnected first and second throughpore sets, each of which comprise a multiplicity of pores for channeling through said matrix a mixture of solutes disposed in a fluid and
surface regions in fluid communication with the members of said second throughpores set which sorb a solute in said mixture
(B) passing a fluid mixture of solutes through said matrix at a fluid flow rate greater than 1000 cm/hr to produce:
convective fluid flow through both throughpore sets
a convective flow velocity through said first throughpores set greater than the fluid flow velocity through said second throughpore set and a Peclet Number greater than 1.0, and
a convective fluid flow velocity through a member of said second throughpore set greater than the diffusion rate of said solute within said member of said second throughpores set, and
(C) passing an eluant through said matrix to elute a fraction rich in a selected one of said solutes.

21. The method of claim 20 wherein step B or C is conducted by passing said fluid mixture or eluant through said matrix at a bed velocity greater than 1500 cm/hr.

22. The method of claim 20 wherein sufficient solute is used in step B to load solute from said fluid mixture onto said surface regions at a ratio of at least 1 mg total solute per ml of matrix per minute.

23. The method of claim 20 wherein step B is conducted at fluid flow velocities through the matrix sufficient to produce a specific productivity of at least 2 mg total protein sorbed per ml of matrix per minute.

24. The method of claim 20 wherein the matrix provided in step A comprises packed particles having a mean diameter greater than 8 $\mu$m, said second throughpore set comprises throughpores within the particles having a mean diameter greater than 2000 Å, and the ratio of the mean diameter of the particles to the mean diameters of the pores is less than 70.

25. The method of claim 20 wherein the ratio of the mean diameters of the particles to the mean diameters of the throughpores is less than 50.

26. The method of claim 20 wherein said surface regions comprise subpores having a mean diameter less than about 700 Å.

27. The method of claim 20 wherein the fluid is passed through the matrix in step B or C at a velocity such that the Peclet number in the throughpores of the second throughpore set is greater than 5.

28. The method of claim 27 wherein the Peclet number in the throughpores of the second throughpores set is greater than 10.

29. A chromatography method comprising the steps of:
(A) forming a chromatography matrix by packing a multiplicity of particles defining throughpores and solute interactive surface regions therewithin; and
(B) passing a fluid mixture including a large biological molecule through said matrix at a velocity sufficient to induce a convective fluid flow rate through said throughpores greater than the rate of molecule diffusion through said throughpores and a Peclet Number greater than 1.0.

30. A chromatography method comprising the steps of:
(A) providing a chromatography matrix defining:
interconnected first and second throughpore sets, the members of said first throughpore set having a greater mean diameter then the members of said second throughpore set, and
surface regions in fluid communication with the members of said second throughpore set which reversibly interact with a large biological molecule, and
(B) passing a fluid mixture of solutes including a said large biological molecule through said matrix at a rate sufficient
to induce convective fluid flow through both said throughpore sets,
to induce a convective flow rate within said second throughpore set greater than the rate of diffusion of said biological molecule within said second throughpore set and to produce in said second throughpore set a Peclet Number greater than 1.0.

31. A chromatography method comprising the steps of
A. providing a chromatography matrix defining:
interconnected first and second throughpore sets, each of which comprise a multiplicity of pores for channelling through said matrix a mixture of solutes including a large biological molecule disposed in a fluid, and
surface regions in fluid communication with the members of the second throughpore set which sorb a said biological molecule in said mixture
B. passing a fluid mixture of solutes including a said biological molecule through said matrix at a fluid flow rate sufficient to produce:
convective fluid flow through both throughpore sets,
a convective fluid flow velocity through said first throughpore set greater than the fluid flow velocity through the second throughpore set and a Peclet Number greater than 1.0, and
a convective fluid flow velocity through a member of said second throughpore set greater than the diffusion rate of said biological molecule within said member of said second throughpore set, to load molecules from said fluid mixture onto said surface regions, and C. passing an eluant through said matrix to elute a fraction rich in a selected one of said biological molecules.

32. The method of claim 31 wherein step B or C is conducted by passing said fluid mixture or eluant through said matrix at a bed velocity greater than 1500 cm/hr.

33. The method of claim 31 wherein steps B or C is conducted by passing said fluid mixture or eluant through said matrix at a bed velocity greater than 1000 cm/hr.

34. The method of claim 31 wherein steps B and C are conducted at fluid flow velocities through the matrix sufficient to produce a specific productivity of at least 1 mg total biological molecule sorbed per ml of matrix per minute.

* * * * *